United States Patent
Yang et al.

(10) Patent No.: US 9,611,354 B2
(45) Date of Patent: *Apr. 4, 2017

(54) BIODEGRADABLE PHOTOLUMINESCENT POLYMERS

(71) Applicant: BOARD OF REGENTS, THE UNIVERSITY OF TEXAS SYSTEM, Austin, TX (US)

(72) Inventors: Jian Yang, University Park, PA (US); Santosh Gautam, Irving, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/863,889

(22) Filed: Sep. 24, 2015

(65) Prior Publication Data
US 2016/0075822 A1    Mar. 17, 2016

Related U.S. Application Data

(63) Continuation of application No. 13/962,476, filed on Aug. 8, 2013, now Pat. No. 9,145,467, which is a (Continued)

(51) Int. Cl.
C08G 63/91    (2006.01)
C08J 5/18    (2006.01)
(Continued)

(52) U.S. Cl.
CPC ............ *C08G 63/914* (2013.01); *A61L 27/18* (2013.01); *A61L 27/3891* (2013.01); *A61L 27/50* (2013.01);
(Continued)

(58) Field of Classification Search
CPC .. C08F 283/00; C08F 283/006; C08F 289/00; C08F 290/00; C08G 18/4236;
(Continued)

(56) References Cited

U.S. PATENT DOCUMENTS 6,136,295 A    10/2000 Edwards et al.
7,345,596 B2    3/2008 Wallach et al.
(Continued)

FOREIGN PATENT DOCUMENTS

WO    WO 01/51027 A2    7/2001
WO    2007143209 A2    12/2007
WO    PCT/US2009/047845    6/2009

OTHER PUBLICATIONS

Wang Y, et al., (2002) A Tough Biodegradable Elastomer. Nature Biotechnology 20: 602-606.
(Continued)

*Primary Examiner* — Ling Choi
*Assistant Examiner* — Gennadiy Mesh
(74) *Attorney, Agent, or Firm* — McCarter & English, LLP

(57) ABSTRACT

Biodegradable photoluminescent polymer (BPLP) which comprises an oligomer synthesized from a multifunctional monomer, a diol, and an amino acid by reacting (i) a multifunctional monomer comprising citric acid or triethyl citrate with (ii) a diol to form a reaction product, and further reacting the reaction product with (iii) an amino acid, wherein the amino acid is linked as a side group to the oligomer backbone. The BPLP of the present invention poses tunable fluorescence emission characteristics and are cell-compatible and biodegradable. The BPLP can serve as both implant materials and bioimaging probes.

20 Claims, 24 Drawing Sheets

Related U.S. Application Data continuation of application No. 13/000,327, filed as application No. PCT/US2009/047845 on Jun. 18, 2009, now Pat. No. 8,530,611.

(60) Provisional application No. 61/074,503, filed on Jun. 20, 2008.

(51) Int. Cl.

| | |
|---|---|
| C08G 18/42 | (2006.01) |
| A61L 27/18 | (2006.01) |
| A61L 27/38 | (2006.01) |
| A61L 27/50 | (2006.01) |
| C08F 283/00 | (2006.01) |
| C08F 289/00 | (2006.01) |
| C08F 290/00 | (2006.01) |
| C08G 18/46 | (2006.01) |
| C08G 18/73 | (2006.01) |
| C08G 63/685 | (2006.01) |
| C12N 5/071 | (2010.01) |

(52) U.S. Cl.
CPC .......... *A61L 27/507* (2013.01); *C08F 283/00* (2013.01); *C08F 283/006* (2013.01); *C08F 289/00* (2013.01); *C08F 290/00* (2013.01); *C08G 18/4236* (2013.01); *C08G 18/4283* (2013.01); *C08G 18/4646* (2013.01); *C08G 18/4676* (2013.01); *C08G 18/73* (2013.01); *C08G 63/6854* (2013.01); *C08G 63/6858* (2013.01); *C08J 5/18* (2013.01); *C12N 5/0691* (2013.01); *C08G 2230/00* (2013.01); *C08J 2367/04* (2013.01); *C12N 2533/30* (2013.01)

(58) Field of Classification Search
CPC ............ C08G 18/4283; C08G 18/4646; C08G 18/4676; C08G 18/73; C08G 2230/00; C08G 63/6854; C08G 63/6858; C08G 63/914; C08J 2367/04
See application file for complete search history.

(56) References Cited

U.S. PATENT DOCUMENTS

| | | | |
|---|---|---|---|
| 8,530,611 | B2 | 9/2013 | Yang et al. |
| 9,145,467 | B2 | 9/2015 | Yang et al. |
| 2002/0015720 | A1 | 2/2002 | Katsarava et al. |
| 2002/0018843 | A1 | 2/2002 | Van Antwerp et al. |
| 2002/0193522 | A1 | 12/2002 | Sun |
| 2007/0009441 | A1 | 1/2007 | Erathodiyil et al. |
| 2007/0282011 | A1 | 12/2007 | Gomurashvili et al. |

OTHER PUBLICATIONS

PCT International Search Report and Written Opinion for PCT/US2009/047845 dated Apr. 23, 2010.
NPL and For Pat Documents filled in parent U.S. Appl. No. 13/000,327.
U.S. Appl. No. 61/074,503, filed Jun. 20, 2008.
Bruggeman, Joost P., et al., "Biodegradable Xylitol-Based Polymers," Adv. Mater., (2008), vol. 9999, 6 pages.
Chiu, Jeng-Jiann, et al., "Shear Strett Inhibits Adhesion Molecule Expression in Vascular Endothelial Cells Induced by Coculture with Smooth Muscle Cells," (2003), vol. 101, pp. 2667-2674.
Coe, Seth, et al., "Electroluminescence from Single Monolayers of Nanocrystals in Molecular Organic Devices," Nature, Dec. 19-26, 2002, vol. 420, pp. 800-803.
Gao, Xiaohu, et al., "In Vivo Molecular and Cellular Imaging with Quantum Dots," Current Opinion in Biotechnology, (2005), vol. 16, pp. 63-72.

Gaumet, Marie, et al., "Fluorescent Biodegradable PLGA Particles with Narrow Size Distributions: Preparation by Means of Selective Centrifugation," International Journal of Pharmaceutics, (2007), vol. 342, pp. 222-230.
Ghoroghcian, P. Peter, et al., "Controlling Bulk Optical Properties of Emissive Polymersomes through Intramembranous Polymer-Fluorophore Interactions," Chem. Mater., (2007), Mar. 20, 1996, vol. 6, pp. 1309-1318.
Huang, Szu-Po, et al., "Deep Blue Electroluminescent Phenylene-Based Polymers," Synthetic Metals, (2007), vol. 157, pp. 863-871.
Isaka, Mitsuhiro, et al., "Experimental Study on Stability of a High-Porosity Expanded Polytetrafluoroethylene Graft in Dogs," Ann. Thorac. Cardiovasc Surg., (2006), vol. 12, pp. 37-41.
Jamieson, Timothy, et al., "Biological Applications of Quantum Dots," (2007), Biomaterials, vol. 28, pp. 4717-4732.
Kaushal, Sunjay, et al., "Functional Small Diameter Neovessels Using Endothelial Progenitor Cells Expanded Ex Vivo," Nat. Med., Sep. 2001, 7(9)1035-1040.
Klimov, V.L., et al., "Optical Gain and Stimulated Emission in Nanocrystal Quantum Dots," Science, (2000), 1 page.
Mancini, Michael C., et al., "Oxidative Quenching and Degradation of Polymer-Encapsulated Quantum Dots: New Insights into the Long-Term Fate and Toxicity of Nanocrystals in Vivo," J. Am. Chem. Soc., (2008), vol. 130, pp. 10836-10837.
Matthew, Jeena Ann, et al., "Nano-Featured Highly Interconnective Macroporous Elastic Scaffolds for Cardovascular Tissue Engineering," IEEE Dallas Engineering in Medicine and Biology Workshop, Nov. 11-12, 2007, 6 pages.
McGonigle, E.A., et al., "Permeability of N2, Ar, He, O2 and CO2 Through Biaxially Oriented Polyester Films—Dependence on Free Volume," Polymer, (2000), vol. 42, pp. 2413-2426.
Michalet, X., et al., "Quantum Dots for Live Cells, in Vivo Imaging, and Diagnostics," Science, Jan. 28, 2005, vol. 307, pp. 538-544.
Nijst, Christiaan L.E., et al., "Synthesis and Characterization of Photocurable Elastomers from Poly(glycerol-co-sebacate)," Biomacromolecules, (2007), 7 pages.
Niklason, Laura E., et al., "Morphologic and Mechanical Characteristics of Engineered Bovine Arteries," J. Vasc. Surg., (2001), vol. 33, pp. 628-638.
Nirmal, Manoj, et al., "Luminescence Photophysics in Semiconductor Nanocrystals," Acc. Chem. Res., (1999), vol. 32, pp. 407-414.
Ogura, Yuichiro, et al., Biodegradable Polymer Microspheres for Targeted Drug Delivery to the Retinal Pigment Epithelium, Survey of Ophthalmology, May 1995, vol. 39, Supplement 1, pp. S17-S24.
Rhymer, Matthew N., et al., "Quantum Dots and Multifunctional Nanoparticles: New Contrast Agents for Tumor Imaging," Nanomedicine, (2006), 9 pages.
Thurn, K. Ted., et al., "Nanopartcles for Applications in Cellular Imaging," Nanoscale Res. Letters, (2007), vol. 2, pp. 430-441.
Timmer, Mark D., et al., "In Vitro Cytotoxicity of Injectable and Biodegradable Poly(propylene fumarate)-Based Networks: Unreacted Macromers, Cross-Linked Networks, and Degradation Products," Biomacromolecules, (2003), vol. 4, pp. 1026-1033.
Wang, Haifeng, et al., "In Vitro and in In Vivo Two-Photon Luminescence Imaging of Single Gold Nanorods," PNAS, Nov. 1, 2005, vol. 102, No. 44, pp. 15752-15756.
Wang, Yadong, et al., "A Tough Biodegradable Etastomer," Nature Biotechnology, Jun. 2002, vol. 20, pp. 602-606.
Woessner, J. Frederick, "The Determination of Hydroxyproline in Tissue and Protein Samples Containing Small Proportions of this Imino Acid," Arch. Biochem. Biophys., (1961), vol. 93, 1 page.
Wozniak, Anna K, et al., "Single-Molecule FRET Measures Bends and Kinks in DNA," PNAS, Nov. 25, 2008, vol. 105, No. 47, pp. 18337-18342.
Xu, Jie, et al., "Tissue-Engineered Vessel Strengthens Quickly Under Physiological Deformation: Application of a New Perfusion Bioreactor with Machine Vision," J. Vasc. Res., (2005), vol. 42, pp. 503-508.
Yang, Jian, et al., "Synthesis and Evaluation of Poly(diol citrate) Biodegradable Elastomers," Biomaterials, (2006), vol. 27, pp. 1889-1898.

(56) References Cited

OTHER PUBLICATIONS

Yang, Jian, et al., "Fabrication and Surface Modification of Macroporous Poly(l-lactic acid) and Poly (L-latic-co-glycolic acid) (70/30) Cell Scaffolds for Human Skin Fibroblase Cell Culture," J. Biomed. Mater Res., (2002), vol. 62, pp. 438-446.

Yang, Jian, et al., "Plasma-Treated, Collagen-Anchored Polylactone: Its Cell Affinity Evaluation Under Shear or Shear-Free Conditions," J. Biomed. Mater Res., (2003), vol. 67A, pp. 1139-1147.

Yang, Jian, et al., "Novel Citric Acid-Based Biodegradable Elastomers for Tissue Engineering," Adv. Mater., Mar. 18, 2004, vol. 16, No. 6, pp. 511-516.

Yang, Jian, et al., "Novel Biphasic Elastomeric Scaffold for Small-Diameter Blood Vessel Tissue Engineering," Tissue Engineering, (2005), vol. 11, No. 11/12, pp. 1876-1886.

Yang, Jian, et al., "Modulating Expanded Polytetrafluoroethylene Vascular Graft Host Response via Citric Acid-Based Biodegradable Elastomers," Adv. Mater., (2006), vol. 18, pp. 1493-1498.

Yang, Jaemoon, et al., "Fluorescent Magnetic Nanohybrids as Multimodal Imaging Agents for Human Epithelial Cancer Detection," Biomaterials, (2008), vol. 29, pp. 2548-2555.

Yanushevich, Yurii G., et al., "A Strategy for the Generation of Non-Aggregating Mutants of Anthozoa Fluorescent Proteins," FEBS Letters, (2002), vol. 511, pp. 11-14.

BIODEGRADABLE PHOTOLUMINESCENT POLYMERS

CROSS-REFERENCE TO RELATED APPLICATIONS

This application is a continuation of U.S. patent application Ser. No. 13/962,476, filed Aug. 8, 2013, now U.S. Pat. No. 9,145,467, which is a continuation of U.S. patent application Ser. No. 13/000,327, filed Apr. 5, 2011, now U.S. Pat. No. 8,530,611, which is a national stage entry application of International Application No. PCT/US2009/047845, filed Jun. 18, 2009, which claims priority of U.S. Application Ser. No. 61/074,503, filed Jun. 20, 2008.

FIELD OF INVENTION

The present invention relates in general to the field of biodegradable polymers, and more particularly to the discovery and manufacture of a novel biodegradable photoluminescent polymer (BPLP) for biomedical applications.

BACKGROUND ART

Without limiting the scope of the invention, its background is described in connection with applications and methods for manufacturing photoluminescent polymers and the use of these polymers in the biomedical fields.

US Patent Application No. 2002/0193522 (Yih-Min Sun, 2002) describes the synthesis and luminescent characteristics of novel phosphorus containing light-emitting polymers, especially one improving the luminescence efficiency of the synthesis light-emitting polymers. According to the method of the present invention, the electron-transporting chromophores are introduced into an emission polymer to increase its electron affinity. Further, several phosphorus-containing emission chromophores are synthesized and incorporated with electron-transporting chromophores finally resulting in the novel phosphorus chromophores emitting blue light as expected, improving thermal stability of resulting polymers such that the absorption peaks of these polymers are restricted to a stable range.

WIPO Patent Application No: WO/2007/143209 (Fraser, et al. 2007) discloses luminescent diketonate polymers having fluorescent properties, phosphorescent properties, or both fluorescent and phosphorescent properties.

U.S. Pat. No. 7,345,596 issued to Wallach and Lincoln, 2008 describes smart polymeric multilayer sensors in the form of beads suitable for submarine detection. The sensors have a change in detectable property, such as color, which occurs when said sensors are exposed to a particular stimulus such as an object or event to be detected. The change in property is thus detectable by an external monitor.

US Patent Application No. 2002/0018843 A1 (Antwerp and Mastrotoaro, 2002) discloses a method for determination of the concentration of biological levels of polyhydroxylated compounds, particularly glucose. The methods utilize an amplification system that is an analyte transducer immobilized in a polymeric matrix, where the system is implantable and biocompatible. Upon interrogation by an optical system, the amplification system produces a signal capable of detection external to the skin of the patient. Quantification of the analyte of interest is achieved by measurement of the emitted signal.

SUMMARY OF THE INVENTION

The present invention includes compositions and methods of making novel aliphatic biodegradable photoluminescent polymers (BPLPs) and their associated crosslinked variants (CBPLPs) for biomedical applications. The BPLPs are degradable oligomers synthesized from biocompatible multifunctional monomers including, e.g., citric acid, aliphatic diols, and various amino acids via a convenient and cost-effective polycondensation reaction. BPLPs can be cross-linked into elastomeric crosslinked polymers, CBPLPs. The present invention includes BPLP linked to amino acids (e.g., (BPLP-cysteine (BPLP-Cys) and BPLP-serine (BPLP-Ser)), which offer advantages over traditional fluorescent organic dyes and quantum dots due to their preliminarily demonstrated cytocompatibility in vitro, minimal chronic inflammatory responses in vivo, controlled degradability and high quantum yields, tunable fluorescence emission, and photostability.

One embodiment of the present invention describes an aliphatic biodegradable photoluminescent polymer (BPLP) composition comprising a degradable oligomer, synthesized from a biocompatible multifunctional monomer, a diol; and an amino acid linked as a side chain to the BPLP backbone. In one aspect the BPLP is optionally post-polymerized by a condensation reaction to form a crosslinked variant (CBPLP). The biocompatible monomer comprises citric acid, the diol comprises 1,8-octanediol, and the amino acid comprises cysteine or serine. In one aspect of the present invention the biocompatible monomer comprises citric acid and the diols comprises saturated aliphatic diols, C3-C12 diols, macrodiols, hydrophilic diols, hydrophobic diols or any combinations thereof. In another aspect the diols are selected from a group comprising of 1,8-octanediols, ethylene glycol, propylene glycol, macrodiols, poly(ethylene glycol), poly(propylene glycol) 1,3-propanediol, ethanediol, and cis-1,2-cyclohexanediol. In yet another aspect the citric acid is at least partially replaced by unsaturated maleic acid or maleic anhydride, fumaric acid, fumaryl chloride, acroylchloride, itaconic acid, and allylmalonic acid monomers to yield an injectable BPLP. In one aspect the BPLP is optionally crosslinked, wherein the crosslinking is achieved by radical polymerization initiated by photoinitiators or redox initiators. The amino acids in the invention are selected from alanine, arginine, asparagine, aspartic acid, cysteine, glycine, glutamine, glutamic acid, histidine, isoleucine, leucine, lysine, methionione, proline, phenylalanine, serine, threonine, tyrosine, tryptophan, valine or any combinations thereof.

In certain aspects the post-polymerization is a polycondensation or a free radical polymerization. The BPLP or the CBPLP of the present invention exhibits a fluorescence wherein the fluorescence emanates from a 6-membered aliphatic and biodegradable ring formed by a carboxylic acid, an alpha carbon, and an amino group of the amino acid. The carboxylic acid, the alpha carbon, and the amino groups bend backwards to join the polymer backbone via an esterification reaction.

Another embodiment of the present invention describes a method of making an aliphatic biodegradable photoluminescent polymer (BPLP) comprising the steps of: (i) mixing a biocompatible multifunctional monomer, a diol, and an amino acid to form a mixture, (ii) raising the temperature of the mixture to melt the mixture, and (iii) lowering the temperature of the mixture with stirring to form the aliphatic BPLP. The method of the present invention further comprises the step of purifying the BPLP by precipitating the BPLP in a solvent mixture or by dialysis. In one aspect the biocompatible monomer used in the method described in the present invention comprises citric acid, the diol comprises 1,8-octanediol, and the amino acid comprises cysteine or serine. The solvent mixture used in the method of the present invention is selected from a group comprising of 1,4-dioxane/water, ethanol/water, acetone/water, and tetrahydrofuran/water.

In the method of the present invention the biocompatible multifunctional monomer and the diol are provided in equal amounts and the biocompatible monomer comprises maleic acid, unsaturated monomers, or citric acid at least partially replaced with unsaturated maleic acid, maleic anhydride, fumaric acid, fumaryl chloride, acroylchloride, itaconic acid, and allylmalonic acid. In yet another aspect the BPLP is injectable.

In yet another embodiment the present invention describes a method of making a cross-linked biodegradable photoluminescent polymer (CBPLP) comprising the steps of: dissolving a biodegradable photoluminescent polymer in an organic solvent to form a solution, casting the solution in a mold, evaporating the solvent, and post-polymerizing the BPLP to forms the CBPLP. The organic solvent used in the manufacture of the CBPLP is selected from a group comprising of 1,4-dioxane, ethanol, acetone, and tetrahydrofuran.

The present invention also discloses a method of making a water soluble aliphatic biodegradable photoluminescent polymer (BPLP) comprising the steps of: (i) mixing equal amounts of citric acid and polyethylene glycol to form a mixture, (ii) adding serine or cysteine to the mixture, (iii) raising the temperature of the mixture to melt the mixture, and (iv) lowering the temperature of the mixture while stirring to form the water soluble BPLP.

In one embodiment the present invention further describes a method of making one or more aliphatic biodegradable photoluminescent polymer (BPLP) nanoparticles comprising the steps of: dissolving a BPLP in an organic solvent to form a solution, adding the solution dropwise to deionized water with stirring, and evaporating the organic solvent to form the one or more aliphatic (BPLP) nanoparticles. In one aspect the BPLP comprises a degradable oligomer synthesized from a biocompatible multifunctional monomer, a diol, and an amino acid, wherein the biocompatible monomer comprises citric acid the diols comprises saturated aliphatic diols, C3-C12 diols, macrodiols, hydrophilic diols, hydrophobic diols or any combinations thereof. In another aspect the amino acids are selected from alanine, arginine, asparagine, aspartic acid, cysteine, glycine, glutamine, glutamic acid, histidine, isoleucine, leucine, lysine, methionione, proline, phenylalanine, serine, threonine, tyrosine, tryptophan, and valine or any combinations thereof. In yet another aspect the one or more aliphatic (BPLP) nanoparticles are fluorescent, wherein the fluorescence emanates from a 6-membered aliphatic and biodegradable ring formed by a carboxylic acid, an alpha carbon, and an amino group of the amino acid. The carboxylic acid, the alpha carbon, and the amino groups bend backwards to join the polymer backbone via an esterification reaction. In a certain aspect the 6-membered ring is a ester-amide ring One embodiment of the present invention is directed towards an urethane-doped biodegradable photoluminescent polyester (UBPLP) composition comprising: a degradable oligomer, wherein the oligomer is synthesized from a biocompatible multifunctional monomer, a diol, an amino acid, and a di-isocyanate wherein the amino acid is linked as a side chain to the BPLP backbone. The biocompatible monomer in the CUBPLP of the present invention further comprises citric acid, the diol comprises 1,8-octanediol, and the amino acid comprises cysteine or serine and the di-isocyanate comprises Hexamethylene-1,6-di-isocyanate (HDI), or 1,4-Butane di-isocyanate (BDI). In one aspect of the present invention the biocompatible monomer comprises citric acid. In another aspect the diols comprises saturated aliphatic diols, C3-C12 diols, macrodiols, hydrophilic diols, hydrophobic diols or any combinations thereof. In yet another aspect the diols are selected from a group comprising of 1,8-octanediols, ethylene glycol, propylene glycol, macrodiols, poly(ethylene glycol), poly(propylene glycol) 1,3-propanediol, ethanediol, and cis-1,2-cyclohexanediol. The amino acids in the CUBPLP are selected from alanine, arginine, asparagine, aspartic acid, cysteine, glycine, glutamine, glutamic acid, histidine, isoleucine, leucine, lysine, methionione, proline, phenylalanine, serine, threonine, tyrosine, tryptophan, valine or any combinations thereof. The di-isocyanates are selected from a group comprising Hexamethylene-1,6-di-isocyanate (HDI), 1,4-Butane di-isocyanate (BDI), lysine di-isocyanate (LDI), or any other di-isocyanates. In a specific aspect the UBPLP exhibits a fluorescence emanating from a 6-membered aliphatic and biodegradable ring formed by a carboxylic acid, an alpha carbon, and an amino group of the amino acid. The carboxylic acid, the alpha carbon, and the amino groups bend backwards to join the polymer backbone via an esterification reaction.

In another embodiment the present invention describes a method of making an a crosslinked urethane-doped biodegradable photoluminescent polyester (CUBPLP) comprising the steps of: (i) mixing a biocompatible monomer and a diol to form a mixture, (ii) raising the temperature of the mixture to melt the mixture, (iii) lowering the temperature of the mixture with stirring to form an oligomer, (iv) adding an amino acid to the oligomer with stirring to form a pre-BPLP-amino acid, (iv) purifying the pre-BPLP-amino acid by dropwise addition to deionized water, (v) collecting an undissolved pre-BPLP-amino acid portion from the deionized water, (vi) lyophilizing the collected pre-BPLP-amino acid to obtain purified pre-BPLP, (vii) dissolving the purified pre-BPLP-amino acid in 1,4-dioxane to form a solution, (viii) adding 1,6-hexamethyl diisocyanate (HDI) to the pre-BPLP-amino acid solution which may optionally contain one or more catalysts to form a pre-CUBPLP (UBPLP), (ix) casting a film of the pre-CUBPLP (UBPLP) in a laminar airflow, and (x) placing the pre-CUBPLP (UBPLP) in an oven to obtain the CUBPLP. The biocompatible monomer used in the manufacture of the CUBPLP comprises citric acid, the diol comprises 1,8-octanediol, and the amino acid comprises cysteine or serine. In one aspect the one or more catalysts are selected from a group comprising tin-based catalysts such as organotin catalysts, tin octanoate (stannous octanoate), dibutyl tin dilaurate and amine catalysts such DABCO (1,4-diazabicyclo[2.2.2]octane).

In yet another embodiment the present invention describes a method for fabricating crosslinked aliphatic biodegradable photoluminescent polymer (CBPLP) scaffolds comprising the steps of: (i) freeze-drying a BPLP solution in a mold and (ii) post polymerizing the freeze-dried solution in an oven to form a CBPLP scaffold.

Yet another embodiment of the present invention is directed towards a method of fabricating a small diameter blood vessel (SDBV) graft, wherein the SDBV graft comprises multiple crosslinked aliphatic biodegradable photoluminescent polymer (CBPLP) scaffolds; comprising the steps of: (i) transferring first cells on a first CBPLP scaffold, (ii) transferring second cells on a second CBPLP scaffold, (iii) culturing the first and second CBPLP scaffolds for at least two days, (iv) providing a CBPLP-ser tube, (v) constructing the SDBV graft by rolling the first CBPLP seeded with the first cell and the second CBPLP scaffold seeded with the second cell with the CBPLP-ser tube sequentially on a rod, (vi) removing the rod to form a tubular graft, (vii) seeding third cells onto the lumen of the tubular graft, (viii) culturing the graft for at least 3 days in a coculture medium, and (ix) assembling the graft in a perfusion bioreactor to form the CBPLP-SDBV graft. The method of fabricating a SDBV as described in the present invention further comprises the steps of: mounting the grafts on one or more hollow posts in the perfusion chamber, pumping a cell-culture medium with pulsing into the chamber; wherein the cell-culture medium is in communication with the grafts, and culturing the grafts for a specified period of time in the cell-culture medium. In one aspect of the method the first cells are human aortic fibroblast (HAFB) cells. In another aspect the second cells are human aortic smooth muscle cells (HASMC) cells. In yet another aspect the third cells are human aortic endothelial cells (HAEC) cells.

In a specific embodiment the present invention details a fluorometric method for the detection of cationic polymers in a sample, wherein the cationic polymer does not have a chromophore or lacks a chromophore absorbing above 200 nm comprising the steps of: (i) mixing the sample comprising the cationic polymer with an aqueous solution of a water-soluble biodegradable photoluminescent polymer (BPLP) or an organic solvent of a water-insoluble BPLP, (ii) forming a complex between the cationic polymer in the sample and the water-soluble or water-insoluble BPLP, (iii) measuring a fluorescence signal emanating from the complex of the cationic polymer with the water-soluble or water-insoluble BPLP, (iv) mixing standard solutions comprising different concentrations of the cationic polymer with the with the water-soluble or water-insoluble BPLP solution, (v) forming complexes between the different concentrations of the cationic polymer and the water-soluble or water-insoluble BPLP, (vi) measuring a fluorescence signal emanating from the complex of the different concentrations cationic polymer with the water-soluble or water-insoluble BPLP, (vii) creating a calibration curve by plotting the fluorescence signal values of the complexes versus the different concentrations of the cationic polymer, and (viii) calculating an unknown concentration of the cationic polymer in the sample based on the calibration curve. In one aspect the cationic polymer is Polyquaternium-1,ω-{4-[tris (2-hydroxyethyl)ammonio]-but-2-enylpoly(dimethylammoniobut-2enyl)}tris(2-hydroxyethyl)ammonium polychloride. In another aspect the fluorescence signal is proportional to the concentration of the cationic polymer in the solution.

BRIEF DESCRIPTION OF THE DRAWINGS

For a more complete understanding of the features and advantages of the present invention, reference is now made to the detailed description of the invention along with the accompanying figures and in which.

DESCRIPTION OF THE INVENTION

Figure 1:
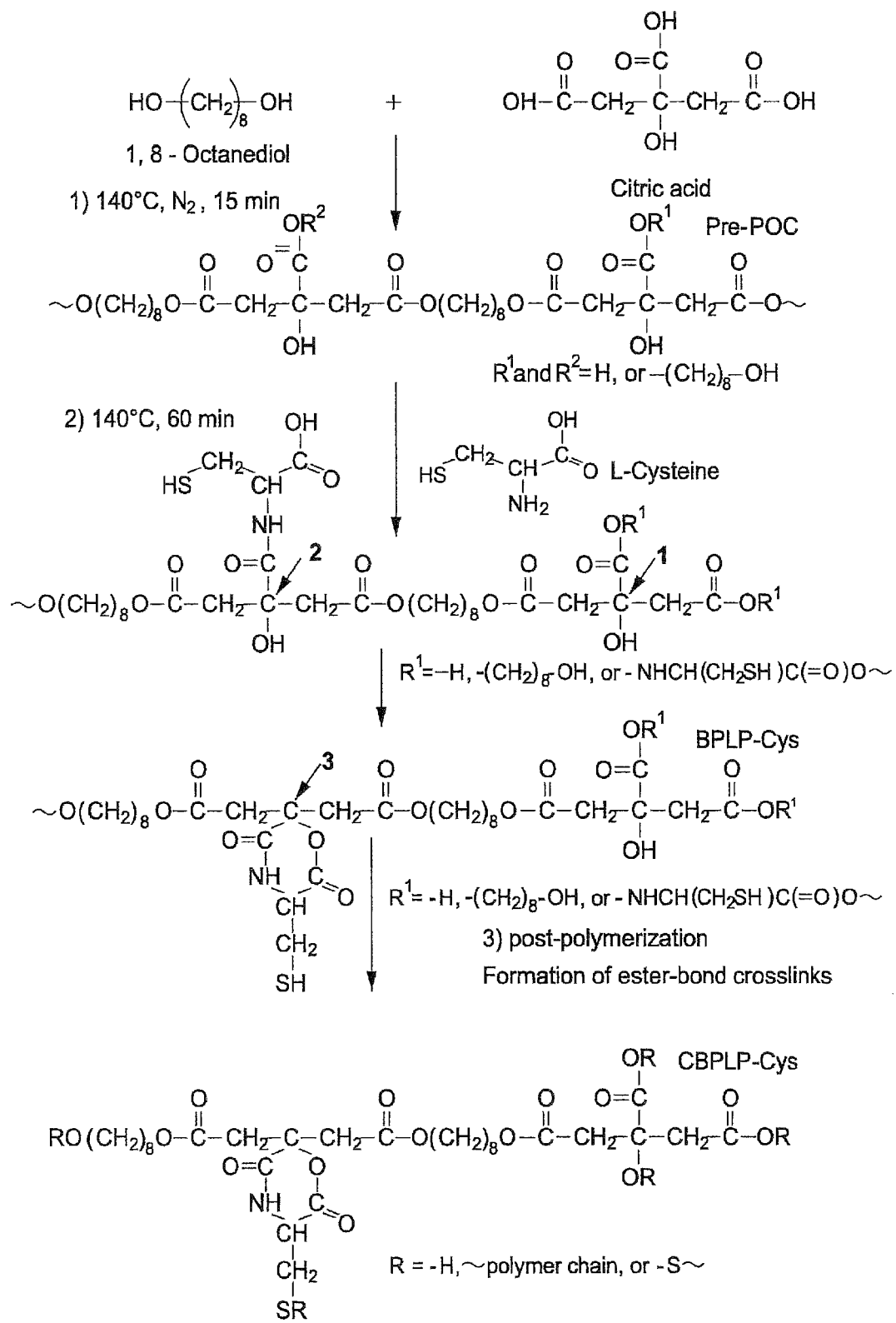
FIG. 1 is a schematic which shows the steps involved in the synthesis of BPLP-Cys.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes the development of novel aliphatic biodegradable photoluminescent polymers (BPLPs) and their associated crosslinked variants (CBPLPs) for biomedical applications. The BPLPs of the present invention are degradable oligomers synthesized from biocompatible multifunctional monomers including citric acid, aliphatic diols, and various amino acids via a convenient and cost-effective polycondensation reaction. The term "multifunctional monomers" as used herein describe monomers including citric acid and its derivatives such as triethyl citrate. The multifunctional monomer such as citric acid can be partially replaced by unsaturated dicarboxyl monomers to make unsaturated BPLPs. The unsaturated carboxylic monomers include but not limited to vinyl-containing maleic acid, maleic anhydride, fumaric acid, fumaryl chloride, and acroylchloride which have at least one carbon-carbon double bonds. The unsaturated BPLPs can be polymerized or crosslinked via radical polymerizations initiated by photoinitiators and/or redox initiators. The unsaturated BPLPs can be further copolymerized or crosslinked with other vinyl-containing monomers such as acrylic monomers. Non-limiting examples of vinyl-containing monomers include acrylates and methacrylates, i.e., diacrylates, triacrylates, dimethacrylates, and trimethacrylates, multifunctional allylic compounds, such as diallyl maleate and allyl methacrylate, multifunctional monomers having a vinyl functionality are also included, allyl methacrylate (AMA), diallyl maleate (DAM), divinyl benzene (DVB), ethylene glycol dimethacrylate (EGDMA), N,N'-methylene-bis-acrylamide (NN-MBA), tripropylene glycol diacrylate (TPGDA), triallyl cyanurate (TAC), triethylene glycol dimethacrylate (TEDMA, TEGMA), trimethylolpropane triacrylate (TMPTA), trimethylolpropane trimethacrylate (TMPTMA, TRIM), and trimethylolpropane diallyl ether (TMPDAE). The diols comprises saturated aliphatic diols including saturated diols such as C3-C12 diols, macrodiols, hydrophilic diols, hydrophobic diols or any combinations thereof, or unsaturated diols such as cis-2-butene-1,4-diol. The amino acids can be L-amino acids, D-amino acids, D,L-amino acids and their derivatives and combinations. BPLPs can be further crosslinked into elastomeric crosslinked polymers, CBPLPs. The inventors in the present disclosure show representatively that BPLP-cysteine (BPLP-Cys) and BPLP-serine (BPLP-Ser) offer advantages over the traditional fluorescent organic dyes and quantum dots due to their preliminarily demonstrated cytocompatibility in vitro, minimal chronic inflammatory responses in vivo, controlled degradability and high quantum yields (up to 62.33%), tunable fluorescence emission (up to 725 nm), and photostability.

The tensile strength of CBPLP-Cys film of the present invention ranged from 3.25±0.13 MPa to 6.5±0.8 MPa and the initial modulus was in the range of 3.34±0.15 MPa to 7.02±1.40 MPa. Elastic CBPLP-Cys could be elongated up to 240±36%. The compressive modulus of BPLP-Cys (0.6) (1:1:0.6 OD:CA:Cys) porous scaffold was 39.60±5.90 KPa confirming the soft nature of the scaffolds. In addition the BPLPs described also possessed great processability for micro/nano-fabrication. The inventors have further shown that the BPLP-Ser nanoparticles ("biodegradable quantum dots") can be used for in vitro cellular labeling and non-invasive in vivo imaging of tissue engineering scaffolds.

None of the current biodegradable polymers can function as both implant materials and fluorescent imaging probes. The development of BPLPs and CBPLPs as described in the present invention represents a new direction in developing fluorescent biomaterials and could impact tissue engineering, drug delivery, bioimaging.

A novel biomaterial may create new fields of study and opportunities to tackle unmet scientific problems. The discovery of fluorescent quantum dots is a good example.[1-4] The unique photoluminescent properties of fluorescent quantum dots brings tremendous opportunities for cancer therapy and diagnosis through biological labeling and imaging. Similarly, fluorescent protein has become one of the most important tools in bioscience, since it can reveal processes previously invisible. Fluorescent biomaterials have been an intense research focus in biomedical and biological fields with wide applications in cellular imaging, biosensing, immunology, drug delivery and tissue engineering.[5-10] Current fluorescent biomaterials include fluorescent organic dyes, fluorescent proteins, lanthanide chelates, and quantum dots. Most of the organic dyes such as fluoresceins, rhodamines, and cyanine dyes are not used in vivo because they exhibit poor photostability and substantial cytotoxicity.[11, 12] Fluorescent proteins often suffer from photobleaching[13, 14] and low quantum yield.[15] Furthermore, the aggregation of fluorescent proteins inside cells may cause cellular toxicity.[16] Although various surface modifications have been attempted to reduce their toxicity,[9, 12, 17, 18] the accumulation of toxic ions released from quantum dots remains a significant concern, especially for long-term use in vivo.

Synthetic fluorescent polymers have been developed for various non-biological applications, such as light emitting diodes.[19] These polymers are not degradable and usually contain conjugated phenyl units raising concerns of potential carcinogenesis or toxicity when used for in vivo biomedical applications. Hitherto, biodegradable fluorescent polymers have required conjugation or encapsulation of the organic dyes or quantum dots on or in the degradable polymers in order to be visualized.[11, 20-23] However, these approaches do not address the previously mentioned drawbacks of the organic dyes and quantum dots. Thus, there is an urgent need for the development of biodegradable and biocompatible photoluminescent materials.

The present invention reports the development of aliphatic biodegradable synthetic polymers, which show intriguing photoluminescence phenomena. A series of novel biodegradable photoluminescent polymers, referred to as BPLPs are described in the present disclosure. BPLPs are low-molecular-weight aliphatic oligomers that include both water-soluble and water-insoluble oligomers. They can be further processed to form elastomeric crosslinked BPLPs (CBPLPs), which not only possess desirable mechanical properties, but also retain strong, tunable fluorescence emission ranging from blue to red. Tunability is afforded by the incorporation of different amino acid residues during polymer synthesis. CBPLPs can be used as implant or device materials and, in addition, as in vivo bioimaging probes. The present invention studies the in vitro cellular uptake of fluorescent BPLP nanoparticles and presents the results of in vivo fluorescence bioimaging of CBPLP scaffolds to demonstrate their potential use in cellular fluorescence labeling, drug delivery and tissue engineering. The present disclosure provides further evidence related to the in vitro degradation and proffer a mechanism through which the photoluminescence of these promising materials are achieved.

Synthesis and Characterization of the BPLP Families:

The synthesis of BPLPs and CBPLPs are straightforward and similar to that for the previously developed biodegradable elastomers, poly(octamethylene citrates) (POC).[24, 25] POC is elastomeric materials. POC porous scaffold is soft (compressive Young's modulus: 0.482 MPa similar to that of many soft tissues in the body[40] and fully elastic (100% recovery after 500 times of cyclic compression). For the synthesis of POC, citric acid (CA) was reacted with 1,8-octanediol (OD) via a condensation reaction to form an oligomer referred to as pre-POC. The pre-POC was then post-polymerized through further condensation to form an elastomeric crosslinked polymer network. Similarly, any of the twenty (enantiomerically-pure (L-)) amino acids were added into the reaction of citric acid and 1,8-octanediol to prepare a family of oligomeric BPLPs such as BPLP-cysteine (BPLP-Cys or POC-Cys) and BPLP-serine (BPLP-Ser or POC-Ser). BPLPs can be optionally further post-polymerized to form CBPLPs. BPLPs are soluble in organic solvents such as 1,4-dioxane, ethanol, acetone, and tetrahydrofuran when hydrophobic diols such as 1,8-octanediol were used. Water soluble BPLPs could be synthesized using hydrophilic diols such as poly(ethylene glycol) (e.g. PEG 200 and PEG 400).

The proposed polymer structures are shown in FIG. 1A. The synthesis of BPLPs is relatively simple. The typical synthesis is described as following: Equimolar amount of citric acid reacted with 1,8-octanediol at 140° C. for 15 min after they were melted at 160° C. in a round-bottom flask then L-cysteine (0.2, 0.4, 0.6 and 0.8 molar ration of cystein/citric acid) was added to the flask to stir for additional 60 min at 140° C. to form a BPLP-cys (or POC-cys) as shown in FIG. 1A. BPLP-cys could be crosslinked via post-polymerization in an oven at 80° C. for 4 days to form crosslinked BPLP-cys (CBPLP-cys or CPOCcys) via the still reactable side and end —COOH and —OH on BPLP-cys.

BPLP-cys can be dissolved in multiple organic solvents such as 1,4-dioxane, ethanol, acetone, tetrahydrofuran (THF) etc. The degradation studies of BPLP-cys and CBPLP-cys confirmed that both polymers are degradable polymers. Modulating the ratio of Lcysteine/citric acid and post-polymerization conditions can adjust degradation of BPLPs and CBPLPs. When poly(ethylene glycol) (PEG, Mw 200 or 400) was added to react with citric acid, water-soluble BPLP-PEG-cys is synthesized. The introduction of PEG was expected to speed up degradation. Thus, the inventors were able to synthesize both water-soluble and organic solvent soluble BPLPs, maximizing the potential of using BPLPs for biological applications. For example, water-soluble BPLPs can be used as fluorescence dye like green fluorescent protein (GFP) or any other water soluble dyes for biological labeling. Water-insoluble BPLPs could be used to fabricate nanoparticles, cell scaffolds for drug delivery and tissue engineering applications. The quantum yields of the BPLP-Cys (62.3%) and BPLP-Ser (26.0%) are much higher than those reported for fluorescent proteins such as green fluorescent protein (GFP) (7.3%) and its blue variants (7.9%) [26,27]. The decay lifetime of BPLP-cys is about 10 ns longer than the common GFP (1.3-3.7 ns)[114, 115].

Figure 2A:
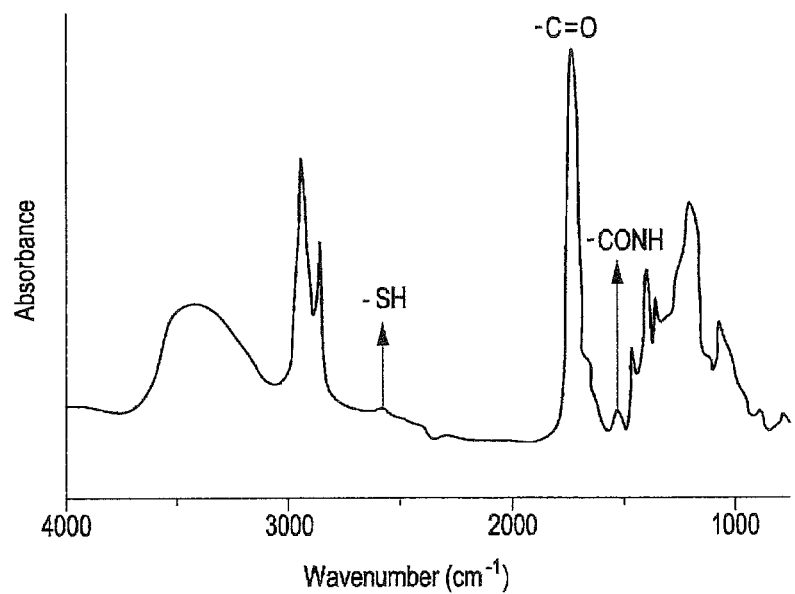
FIG. 2A shows the FTIR spectra of BPLP-Cys (POC-Cys) as a representative BPLP.
Figure 2B:
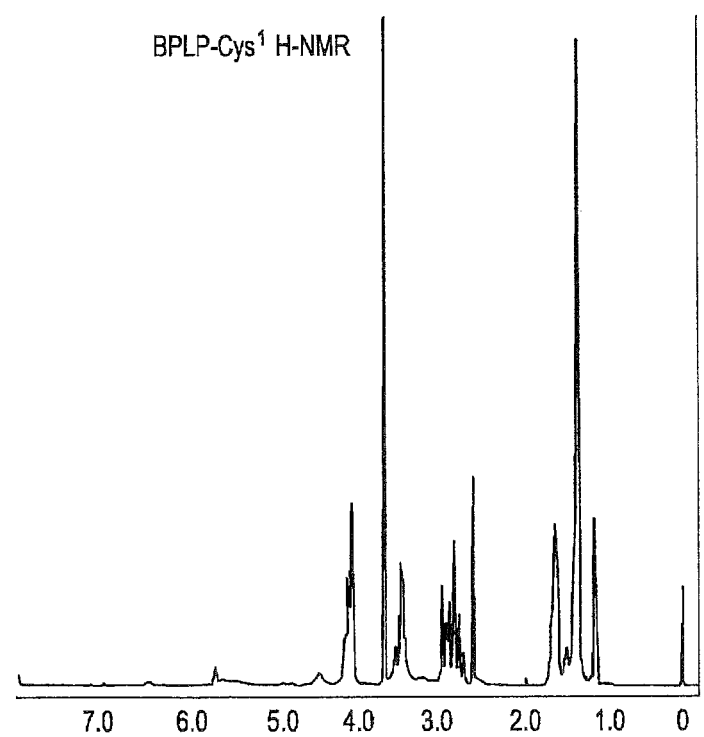
FIG. 2B shows the $^1$H-NMR spectra of BPLP-Cys as a representative BPLP.
Figure 2C:
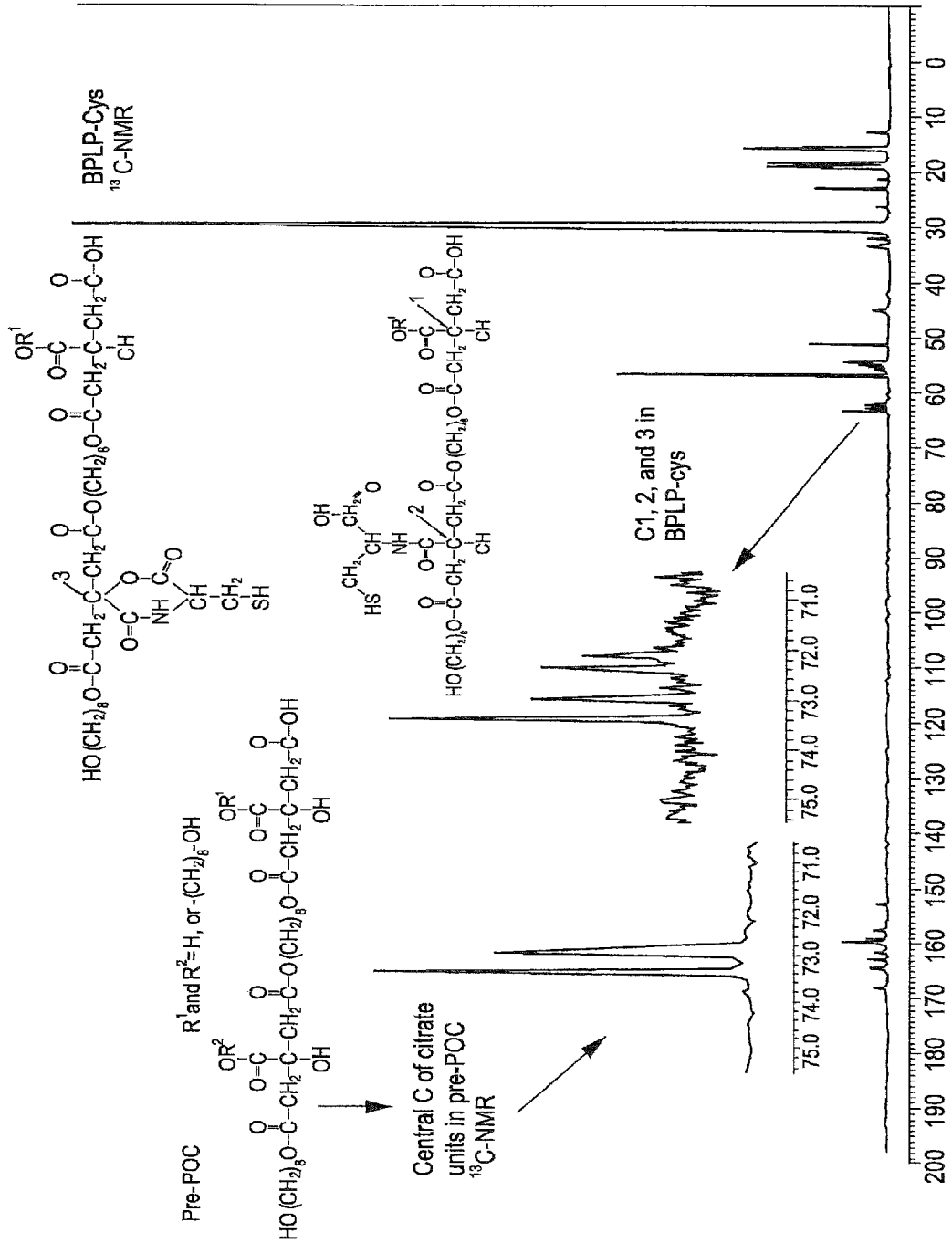
FIG. 2C shows the $^{13}$C-NMR spectra of BPLP-Cys as a representative BPLP.

Polymer characterizations were conducted for BPLP-Cys as a representative BPLP, except where otherwise specified (FIGS. 2A to 2C). For Fourier Transform Infrared (FT-IR) analysis, purified BPLP was dissolved in 1,4-dioxane to make a 5 wt % solution. The BPLP solution was cast onto KBr pellets and the solvent was evaporated overnight. FT-IR spectra were collected at room temperature using a Nicolet 6700 FTIR spectrometer (Thermo Fisher Scientific). For nuclear magnetic resonance (NMR) analysis, 5 mg of polymer was dissolved in 1 ml of deuterated dimethyl sulfoxide (DMSO-$d_6$). The $^1$H-NMR was recorded at room temperature on a JEOL 300 MHz spectrometer, whereas the $^{13}$C-NMR was recorded on a JEOL 500 MHz spectrometer. Tetramethylsilane was used as internal reference in both cases. For matrix-assisted laser desorption/ionization mass spectroscopy (MALDI-MS) analysis, the polymer was ionized with the use of a α-cyano cinnimate N,N-diisopropylethylammonium ionic liquid polymer matrix.

Figure 3A:
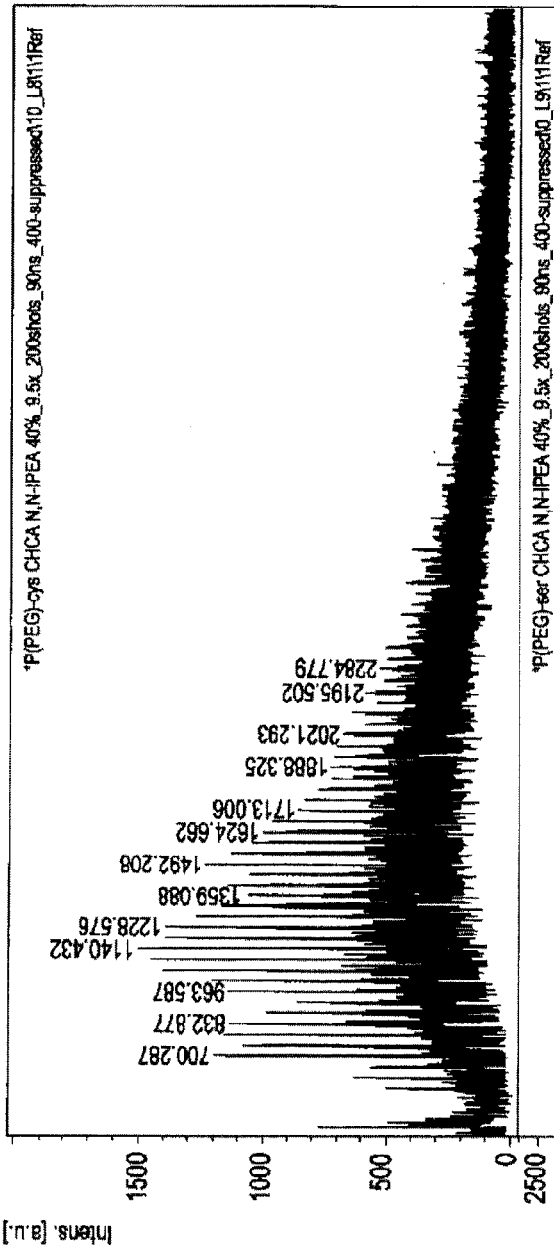
FIG. 3A shows the MALDI-MS spectra used to determine the molecular weight of BPLP-Cys 0.2 (the number average molecular weight was 1334 Da)
Figure 3B:
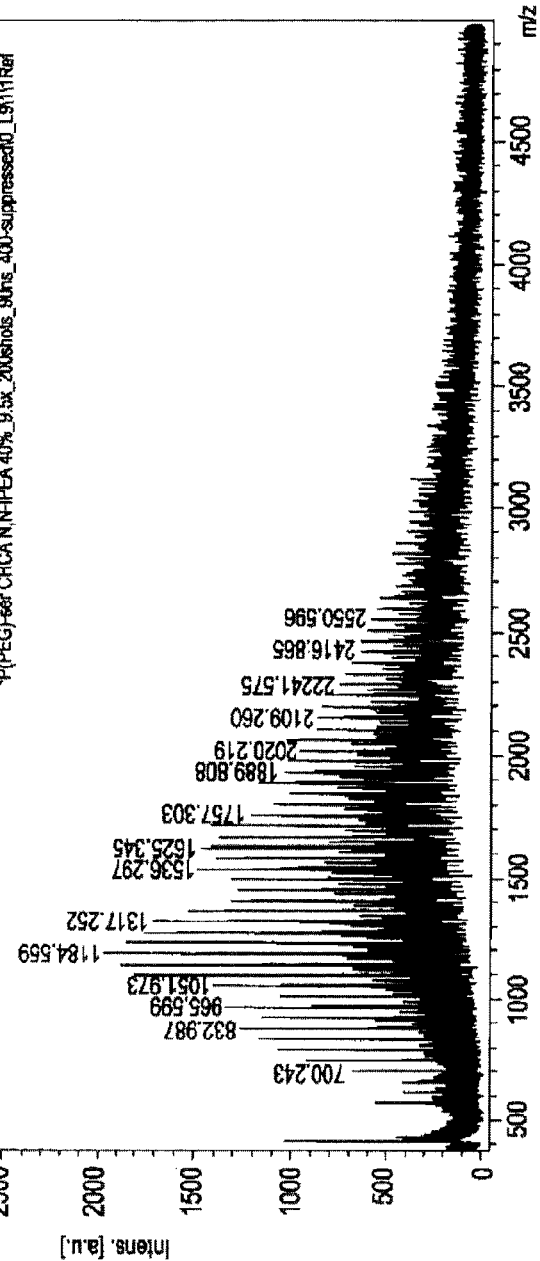
FIG. 3B shows the MALDI-MS spectra used to determine the molecular weight of BPLP-Ser 0.2 (the number average molecular weight was 1459 Da)

The FTIR spectra (FIG. 2A) confirmed the presence of —SH at 2575 $cm^{-1}$, —C(=O)NH— at 1527 $cm^{-1}$, —C=O at 1731 $cm^{-1}$, —$CH_2$— at 2931 $cm^{-1}$, and —OH at 3467 $cm^{-1}$. In the $^1$H-NMR spectra of BPLP-Cys (FIG. 2B), the presence of the peaks at 1.02 ppm (—$CH_2$S$\underline{H}$ from L-cysteine), 1.23 ppm and 1.50 ppm (—C$\underline{H}_2$— from 1,8-octanediol), and the multiple peaks at 2.75 ppm (—C$\underline{H}_2$— from citric acid) confirmed the incorporation of L-cysteine into pre-POC. In the $^{13}$C-NMR spectra of BPLP-Cys (FIG. 2C), the peaks around 170 ppm were assigned to carbonyl ($\underline{C}$=O) groups from citric acid and L-cysteine. The peaks around 63.8 ppm and 28.5 ppm were assigned respectively to —O—CH₂CH₂— and —O—CH₂CH₂— from 1,8-octanediol. The —C(=O)—CH₂— carbon from citric acid was assigned to the peak at 61.2 ppm. The —HN—CH— carbon from L-cysteine was assigned to the peak at 54.5 ppm. There were four peaks assigned to the central carbon atoms of citrate units in various chemical environments. Peaks at 72.9 and 73.4 were assigned to C1 when $R^1$ is —(CH₂)₈—OH and —H respectively. Peaks at 72.1 and 72.4 ppm were assigned to C2 and C3 respectively. However, the $^{13}$C-NMR of pre-POC only showed two peaks of central C of citrate units at 72.9 and 73.4 ppm. The $^{13}$C-NMR results suggest the presence of a 6-membered ring with conjugated character formed on BPLP-Cys as depicted in FIG. 1A. A 6-membered ring formed between L-cysteine and hydroxyl groups on the central C of the citrate unit is proposed to be responsible for the fluorescence as discussed below. The average molecular weight of BPLP-Cys0.2 (formed by reaction of 1:1:0.2 OD:CA:Cys) measured by MALDI-MS was 1334 Dalton (FIG. 3). The above polymer characterization confirmed that L-cysteine was incorporated into the BPLP-Cys. The overall BPLP synthesis is believed to have resulted in a blend of oligomers of POC (pre-POC) and BPLP-Cys as shown in FIG. 1A due to the low percentage of L-cysteine in the polymers.

Figure 4A:
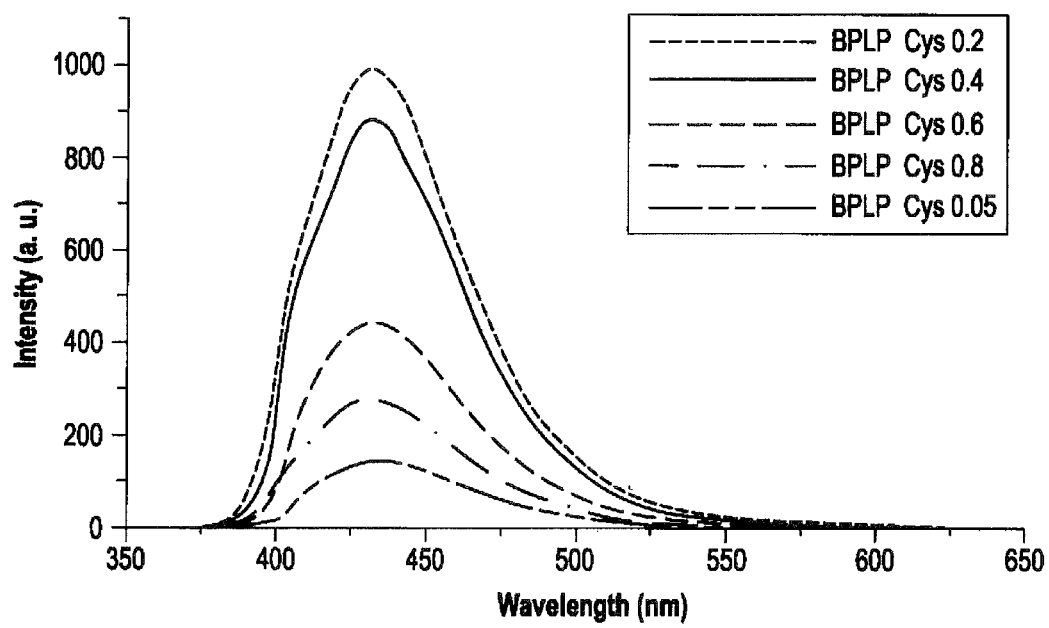
FIG. 4A shows the photoluminescence (PL) emission spectra of BPLP-Cys solution in 1,4-dioxane with various molar ratios of L-cysteine excited at 350 nm.
Figure 4B:
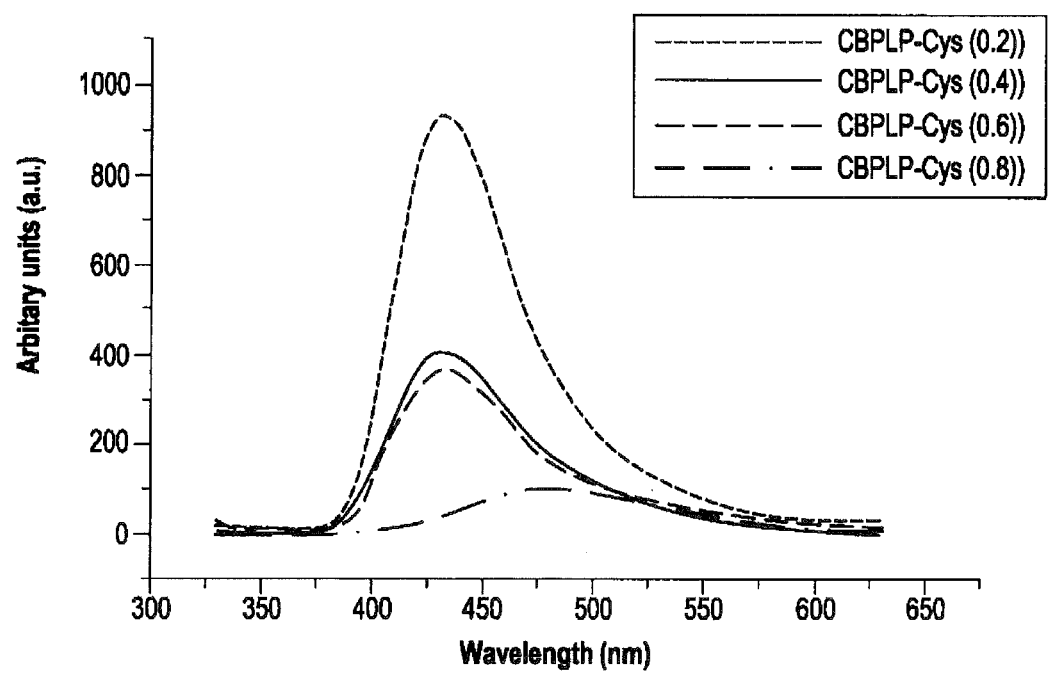
FIG. 4B shows the PL emission spectra of CBPLP-Cys film with various molar ratios of L-cysteine excited at 350 nm.
Figure 4C:
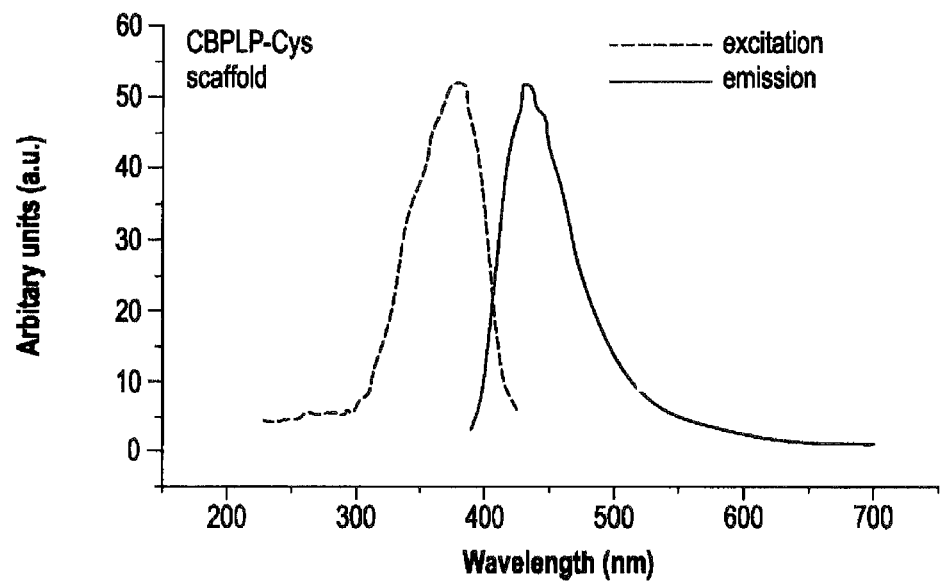
FIG. 4C shows the PL excitation and emission spectra of BPLP-Cys 0.2 porous scaffold)
Figure 4D:
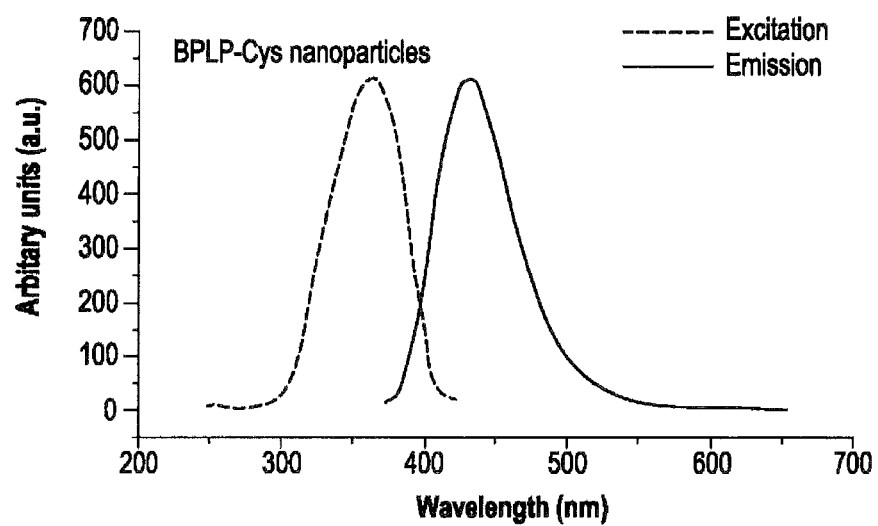
FIG. 4D shows the PL excitation and emission spectra of BPLP-Cys-0.2 nanoparticles (average diameter is 80 nm) (various forms of BPLP-Cys all emit strong fluorescence)
Figure 4E:
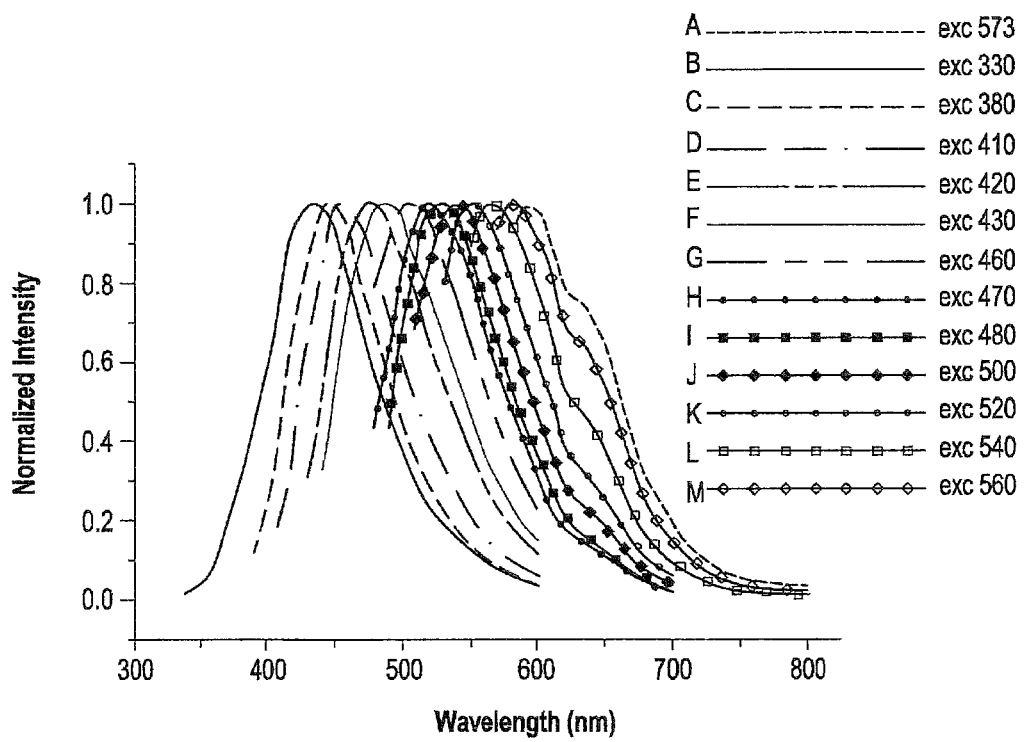
FIG. 4E shows the PL emission spectra of BPLP-serine-0.2 (BPL-Ser-0.2)

Photoluminescence Properties of BPLPs and CBPLPs:

The various forms of BPLPs, including BPLP solution (FIG. 4A), CBPLP films (FIG. 4B), CBPLP scaffolds (FIG. 4C), and BPLP nanoparticles (FIG. 4D), all emit strong fluorescence. The fluorescence intensity of BPLP-Cys can be tuned by varying the molar concentration of L-cysteine in the polymers (FIG. 4A). FIG. 4E shows that BPLP-serine (BPLP-Ser) emits different fluorescent colors from blue to red depending on the excitation wavelength. To further explore this class of material, the inventors synthesized a family of BPLPs using each of the 20 natural amino acids. The BPLPs were found to exhibit fluorescence colors ranging from blue to red (up to 725 nm) (Table 1) depending on the choice of amino acid.

All photoluminescence spectra were acquired on a Shimadzu RF-5301 PC fluorospectrophotometer. Both the excitation and the emission slit widths were set at 1.5 nm for all samples unless otherwise stated. BPLP solutions (5% w/w) in 1,4-dioxane were loaded in a quartz cuvette with a pathlength of 10 mm. To collect the excitation and emission spectra for scaffolds and films (size of about 12 mm×40 mm), samples were held diagonally in a quartz cuvette with a pathlength of 10 mm. The quantum yields of the BPLP polymers were measured by the Williams' method. Briefly, 5% BPLP-Cys 0.2 solution was prepared. The solution was scanned at various excitation wavelengths. Optimal excitation wavelength was determined as the one which generated the highest emission intensity. Then, UV-vis absorbance spectrum was collected with the same solution and the absorbance at the optimal excitation wavelength was noted. Then, a series of solution was prepared with gradient concentration, so that the absorbance of the each solution was within the range of 0.01-0.1 Abs units. The fluorescence spectrum was also collected for the same solution in the 10 mm fluorescence cuvette. The fluorescence intensity, which is the area of the fluorescence spectrum, was calculated and noted. Five solutions with different concentrations were tested and the graphs of integrated fluorescence intensity vs. absorbance were plotted. The quantum yields of the BPLP polymers were calculated according to equation (1) where, Φ=quantum yield; Slope=gradient of the curve obtained from the plot of intensity versus absorbance; η=Refractive index of the solvent; x=subscript to denote the sample, and ST=subscript to denote the standard.

$$\Phi_X = \Phi_{ST}\left(\frac{\text{Slope}_X}{\text{Slope}_{ST}}\right)\left(\frac{\eta_X}{\eta_{ST}}\right)^2 \qquad (1)$$

Anthracene (quantum yield=0.27 in ethanol) was used as a standard. The BPLP polymers were dissolved in 1,4-dioxane and anthracene was dissolved in ethanol. The slit width was kept same for both standard and samples. Absorbance was measured using a SHIMADZU UV-2450 spectrophotometer.

Figure 4F:
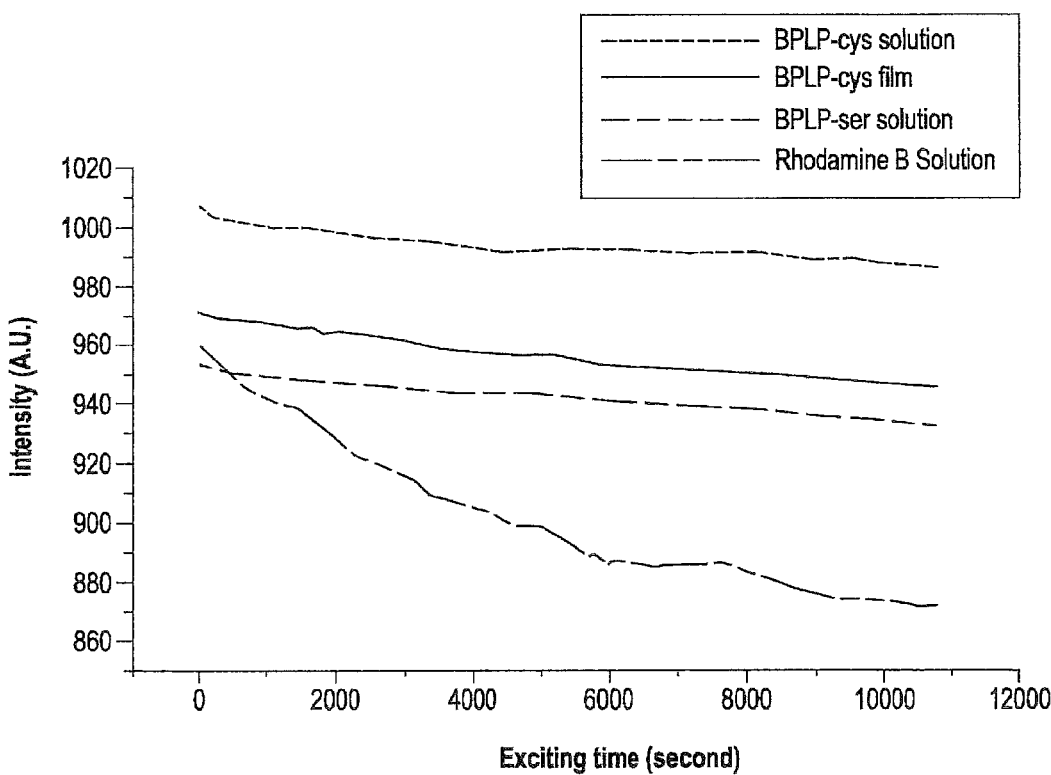
FIG. 4F shows the photostability evaluation of BPLP-Cys0.2 solution and film, BPLP-Ser0.2 solution and control organic dye Rhodamine B.
Figure 4G:
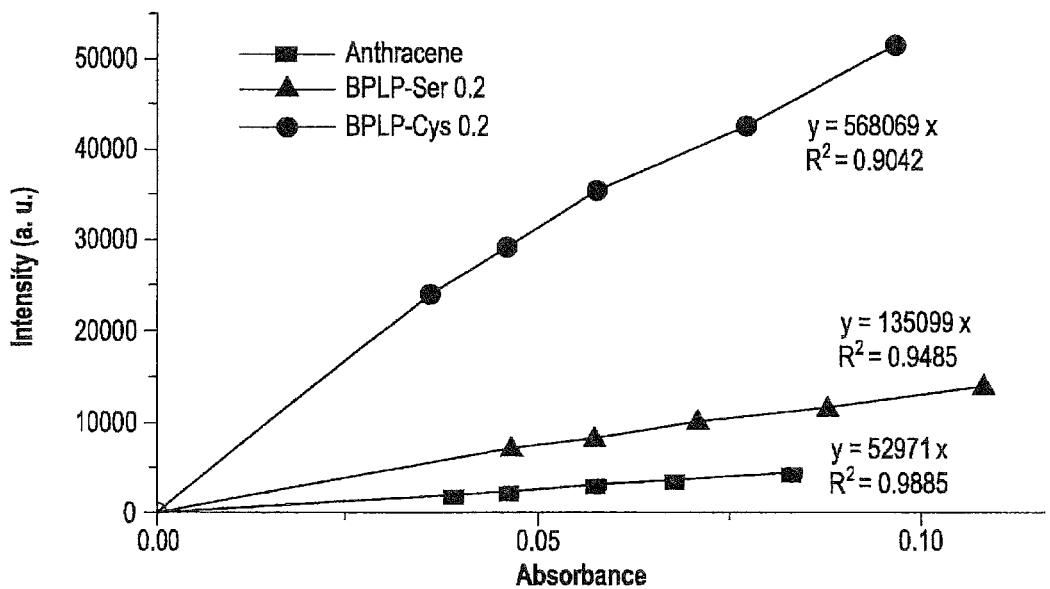
FIG. 4G shows the intensity-absorbance curve of BPLP-Cys for quantum yield measurements.

The fluorescence intensity of BPLP-Cys decreased only slightly (<2%) after continuous UV excitation for 3 hrs indicating excellent photostability as compared to the organic fluorescent dye rhodamine-B (FIG. 4F). The quantum yields of the BPLP-Cys (62.3%) and BPLP-Ser (26.0%) (FIG. 4G and Table 1) were much higher than those reported for fluorescent proteins such as green fluorescent protein (GFP) (7.3%) and its blue variants (7.9%).[15] The emission range and quantum yields of all BPLPs are listed in Table 1.

TABLE 1

Range of excitation and emission wavelengths and quantum yields for BPLPs with twenty different L-amino acids. BPLP-amino acid solutions (1% w/w in 1,4-dioxane) were used for photoluminescence characterization.

| BPLP- | Exc (nm) | Emi (nm) | Quantum Yield (%) |
|---|---|---|---|
| Ala | 250-413 | 295-524 | 5.3 |
| Arg | 250-503 | 297-594 | 0.9 |
| Asn | 280-490 | 299-623 | 11.0 |
| Asp | 275-415 | 301-493 | 11.4 |
| Cys | 240-420 | 312-561 | 62.3 |
| Glu | 255-415 | 296-647 | 0.3 |
| Gln | 280-500 | 296-647 | 13.9 |
| Gly | 265-510 | 295-678 | 10.9 |
| His | 310-540 | 330-650 | 1.9 |
| Ile | 250-403 | 291-499 | 1.2 |
| Leu | 275-415 | 311-525 | 1.0 |
| Lys | 265-535 | 291-646 | 9.4 |
| Met | 250-396 | 286-491 | 0.5 |
| Phe | 270-420 | 294-498 | 0.8 |
| Pro | 255-450 | 294-533 | 0.4 |
| Ser | 290-660 | 303-725 | 26.0 |
| Thr | 250-470 | 313-580 | 34.2 |
| Trp | 300-490 | 340-588 | 12.1 |
| Tyr | 240-440 | 311-561 | 3.1 |
| Val | 240-391 | 279-495 | 1.0 |

Figure 5A:
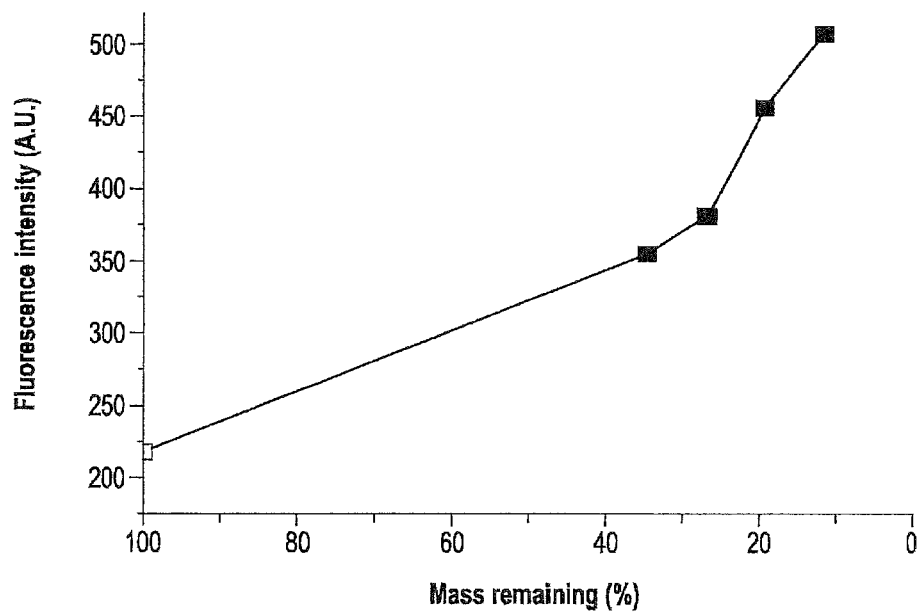
FIG. 5A shows the fluorescence intensity changes over mass remaining for BPLP-Cys0.2 exposed to 0.05M NaOH.
Figure 5B:
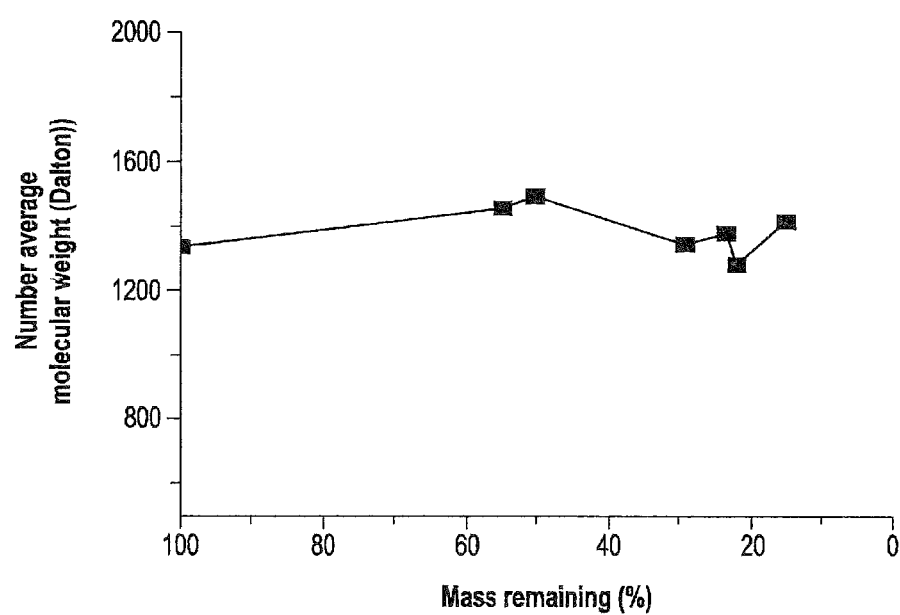
FIG. 5B shows the molecular weight changes over mass remaining for BPLP-Cys0.2 exposed to 0.05M NaOH.

BPLP-Cys was degraded in 0.05 M NaOH solution. Fluorescence intensity was based on the same concentration of BPLP-Cys in 1,4-dioxane at various degradation degrees. Molecular weight was determined by MALDI-MS. The fluorescence intensity of BPLP-Cys0.2 increased with increasing degradation in NaOH solution (FIG. 5A). It should be noted that the fluorescence measurements for polymers under degradation were based on the same concentration of BPLP-Cys in 1,4-dioxane at various degrees of degradation. MALDI-MS analysis indicated that the molecular weight of the insoluble polymer did not significantly change during degradation in NaOH solution (FIG. 5B). This is due to the fact that the polymers containing fluorescent ring-structures may degrade more slowly than the polymers without the ring-structures (pre-POC) due to the relatively higher stability of the amide bonds in the ring-structures. Considering that the molecular weight of pre-POC (Mn=1088 Da)[25] is close to that of Mw of the resulting BPLP-Cys which may contain pre-POC, the degradation may result in an erosion on the pre-POC first, leaving behind the low percentage of BPLP-Cys without significant molecular weight changes. Therefore, the polymer degradation is proposed to have resulted in an increasing concentration of the polymer chains with the fluorescent ring-structures.

Figure 4H:
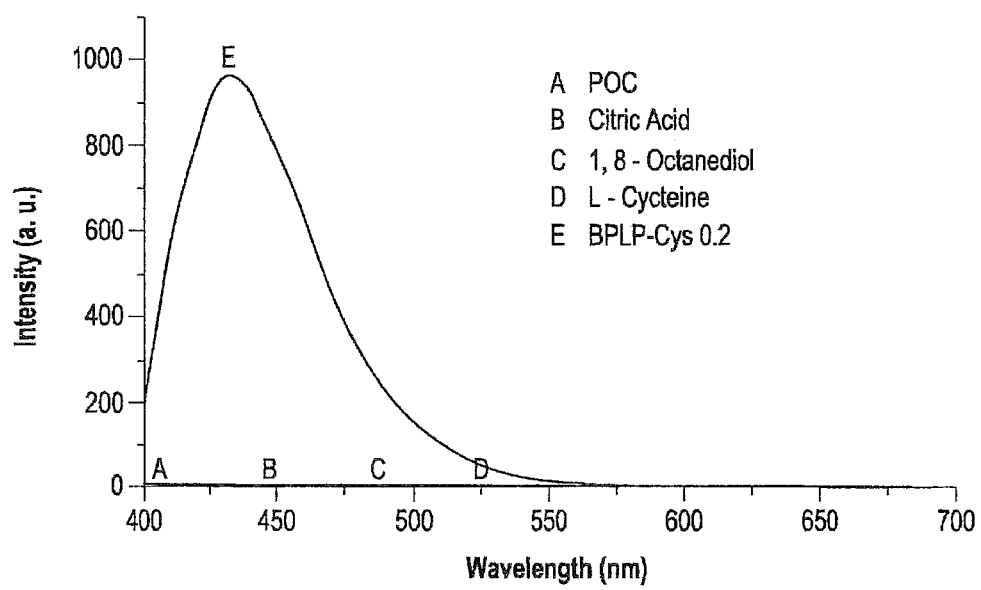
FIG. 4H shows the PL emission spectra of BPLP-Cys, POC and all the monomers used for BPLP-Cys synthesis.

Exploration of the Fluorescence Mechanism:

The potential mechanisms for the fluorescence and the intriguing photoluminescent properties of the BPLP polymers of the present invention were further explored by the inventors. As shown in FIG. 4H, monomers of citric acid, 1,8-octanediol, and L-cysteine emitted only very weak autofluorescence. The POCs synthesized from citric acid and 1,8-octanediol also emitted negligible photoluminescence. However, when L-cysteine was incorporated into POC (BPLP-Cys), a strong fluorescence signal was observed. The inventors attempted to directly synthesize polymers from citric acid and L-cysteine or 1,8-octanediol and L-cysteine, but failed since the melting point of L-cysteine (220° C.) was much higher than the decomposition temperature of citric acid (175° C.). However, when 1,8-octanediol was reacted first with citric acid, the formed pre-POC could then dissolve L-cysteine at 160° C. to form BPLP-Cys. It is reasonable to suggest that during this synthesis the L-cysteine might be either incorporated in the pre-POC backbone or appended to the pre-POC side chains. In order to determine which addition was responsible for the observed fluorescence, a BPLP polymer was synthesized in the presence of succinic acid, instead of citric acid. The resulting polymers emitted only very weak auto-fluorescence. Succinic acid is a diacid, and lacks the additional carboxylic acid and hydroxyl units found in citric acid. Thus, with succinic acid, the side addition of L-cysteine was not possible, supporting the hypothesis that the side addition of L-cysteine to citrate units was an essential step in the formation of fluorescent polymer.

As a possible mechanism, but not a limit the inventors suggest that L-cysteine first covalently links to the carboxylic acid on citrate to form an amide bond through its N-terminus. In a second step, the 6-membered ring is formed by an esterification reaction between the free carboxylic acid on the appended cysteine and the geminal hydroxyl unit remaining on citrate (FIG. 1A). Since all BPLPs with all 20 α-amino acids generate significant fluorescence (Table 1), the formation of a cyclic structure in this manner is consistent with the experimental data, regardless of the different functional units present on the amino acid side chains.

Figure 9:
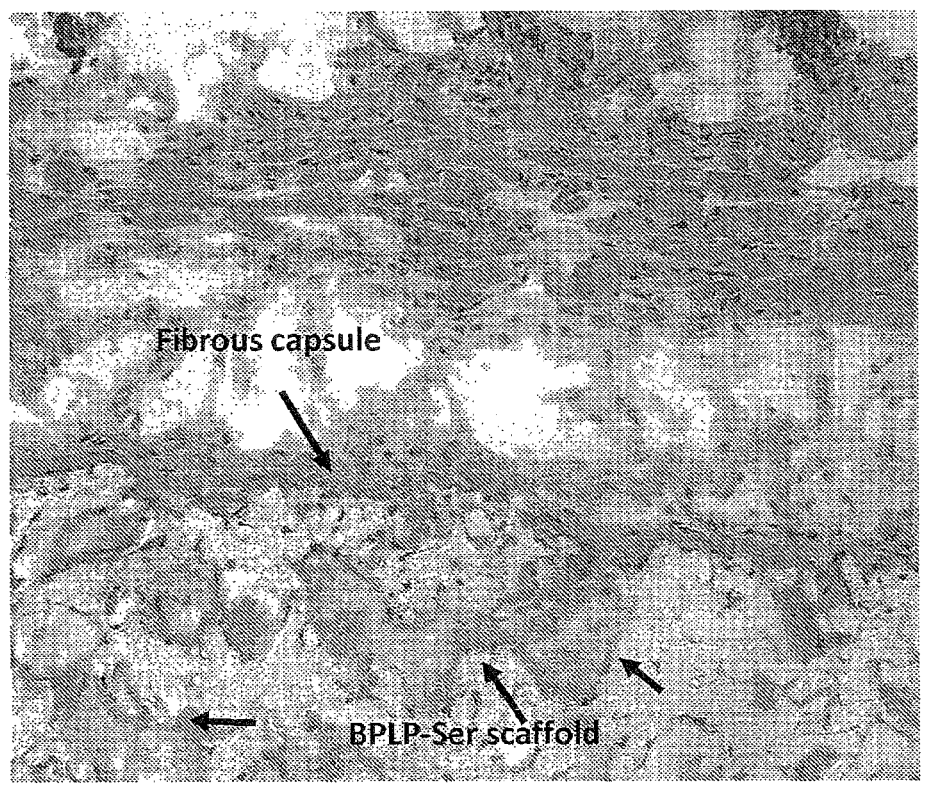
FIG. 9 shows the H&E staining image (100×) for BPLP-Ser0.2 scaffolds implanted into nude mice for 5 months.

It is well known that conjugated systems can emit fluorescence. The fluorophore of current synthetic fluorescent polymers mostly consists of nondegradable units containing conjugated phenyl groups or alternating single and multiple bonds in the polymer chain thus makes them unsuitable for in vivo biomedical applications. It has been reported in an early work that the fluorescence of polymers may arise from the conjugated system by the cyclization of polymer side chain.[41] Highly conjugated system may emit strong fluorescence. POC and L-cysteine themselves only emits very weak autofluorescence. The intermolecular hydrogen bonding of BPLP-cys forming conjugated 6-member ring systems result in the strong fluorescence emitting properties as shown in FIG. 9. The 6-membered rings in the BPLPs are composed of amide and ester bonds with different pendant groups from various amino acids. Amide bonds and ester bonds are resonance stabilized so that the lone pairs on the N and O occupy p-orbitals which conjugate with the p-orbitals on the C=O. Hyperconjugation theory[26] suggests that the electrons in the C—C bond (σ-bond) at the central C3 and the C—H or C—C bond (σ-bond) at the α-C in the amino acids in the 6-membered rings can strongly associate with p-orbitals in the neighboring C=O, N and O to extend the conjugated system throughout the ring. The side chain R groups pendant to the α-C in the amino acids likely influence the degree of hyperconjugation and propensity for cyclization, providing slight perturbations in the associated energy levels and resulting in the different emission maxima and quantum yields observed for the various BPLP-amino acids (Table 1).

Figure 6A:
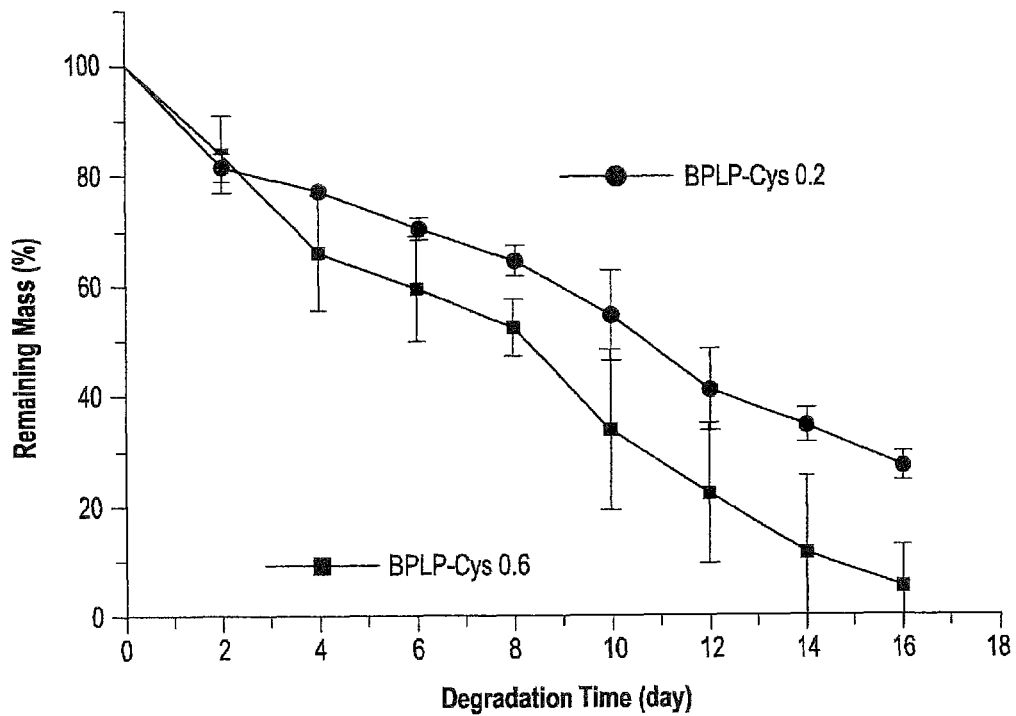
FIG. 6A shows the in vitro degradation of BPLP-Cys in PBS (pH=7.4) at 37° C. (n=5)
Figure 6B:
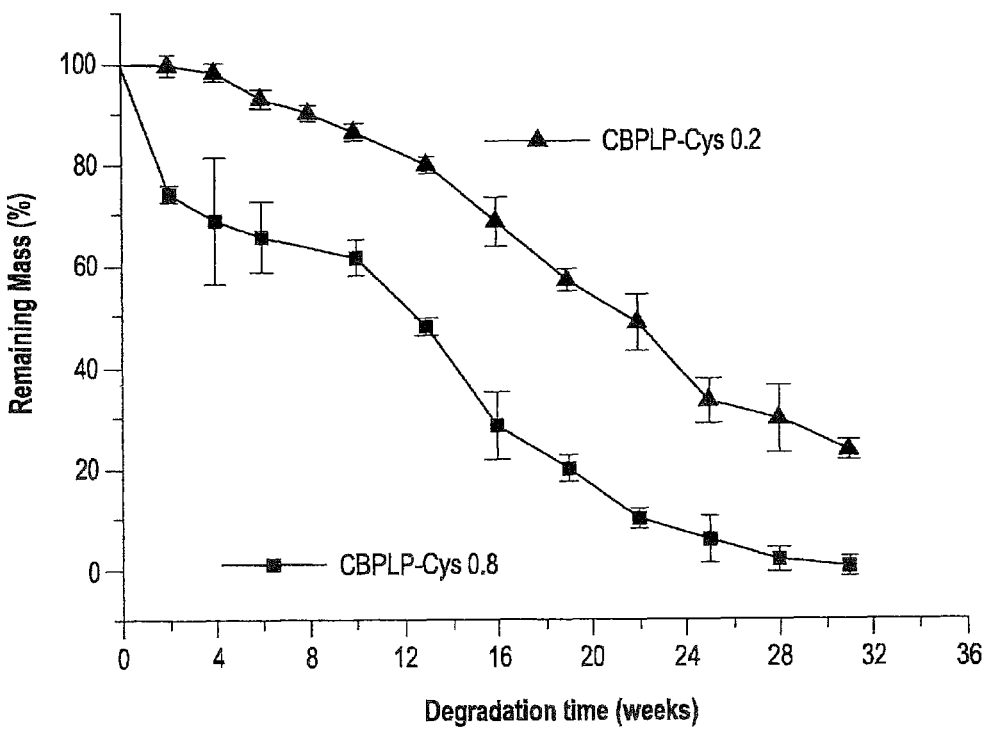
FIG. 6B shows the in vitro degradation of CBPLP-Cys in PBS (pH=7.4) at 37° C. (n=5)

Degradation and Mechanical Properties of BPLP Families:

The degradation rate of BPLP families was found to depend on the ratio of the monomers and the polymerization conditions (FIGS. 6A and 6B). Analysis of soluble in vitro degradation products derived from BPLP-Cys and BPLP-Ser by high performance liquid chromatography—electrospray ionization—mass spectrometry (HPLC-ESI-MS) revealed the presence of a large amount of citrate, in addition to other soluble oligomers (FIG. 7) indicating that the primary degradation mechanism for the polymer in vitro is a return to monomeric material.

Figure 7A:
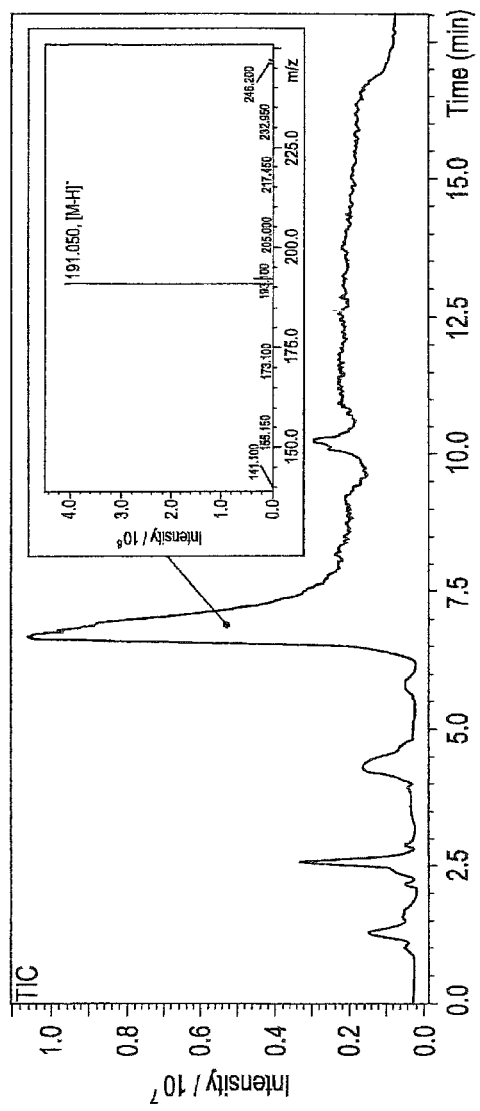
FIG. 7A shows the HPLC-ESI-MS analysis of soluble in vitro degradation products for BPLP-Cys degraded in 0.05 M NaOH for 24 hours.
Figure 7B:
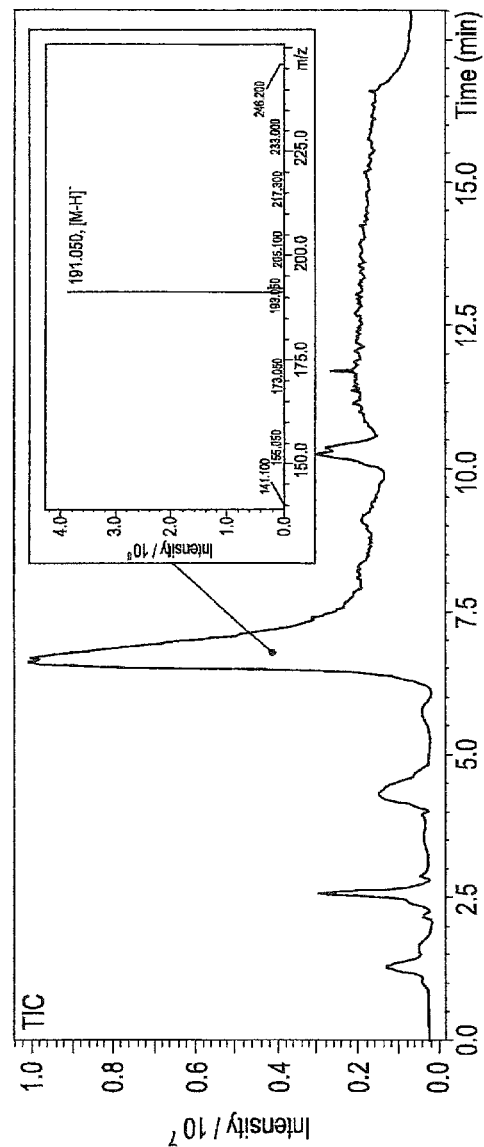
FIG. 7B shows the HPLC-ESI-MS analysis of soluble in vitro degradation products for BPLP-Ser degraded in 0.05 M NaOH for 24 hours.
Figure 8A:
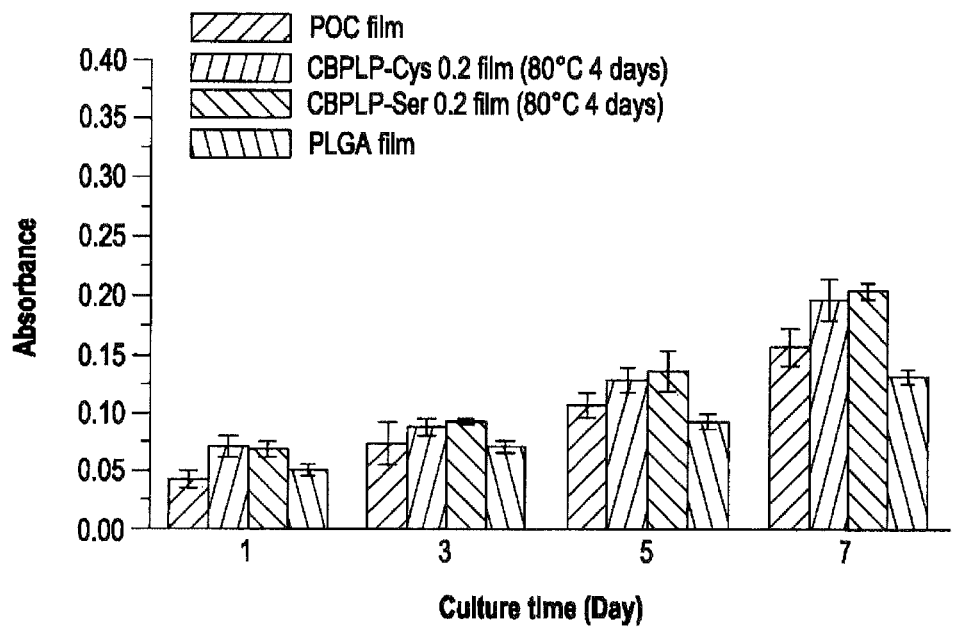
FIG. 8A shows the cell viability and proliferation assay (MTT assay) for 3T3 fibroblasts cultured on BPLP-Cys film with POC and PLGA used as controls.
Figure 8B:
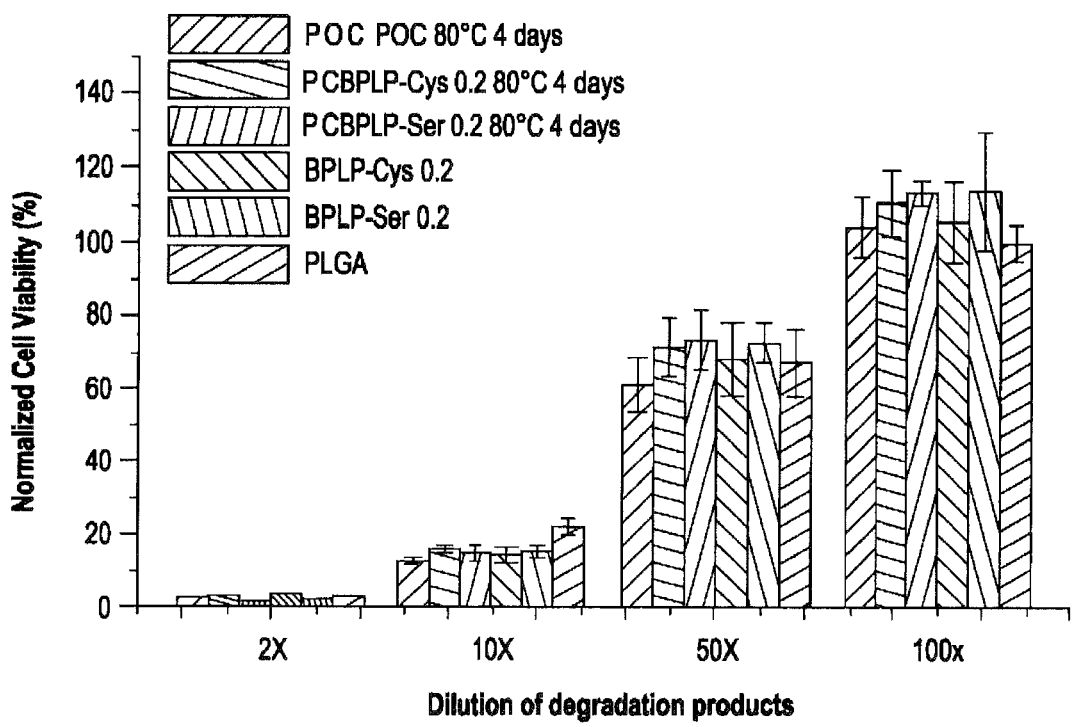
FIG. 8B shows the cytotoxicity evaluation of degradation products of BPLPs (-Cys and -Ser) and CBPLPs (-Cys and -Ser) at 2×, 10×, 50× and 100× dilutions with POC and PLGA75/25 used as controls (all data were normalized to the mean absorbance of PLGA (100× dilution))
Figure 8C:
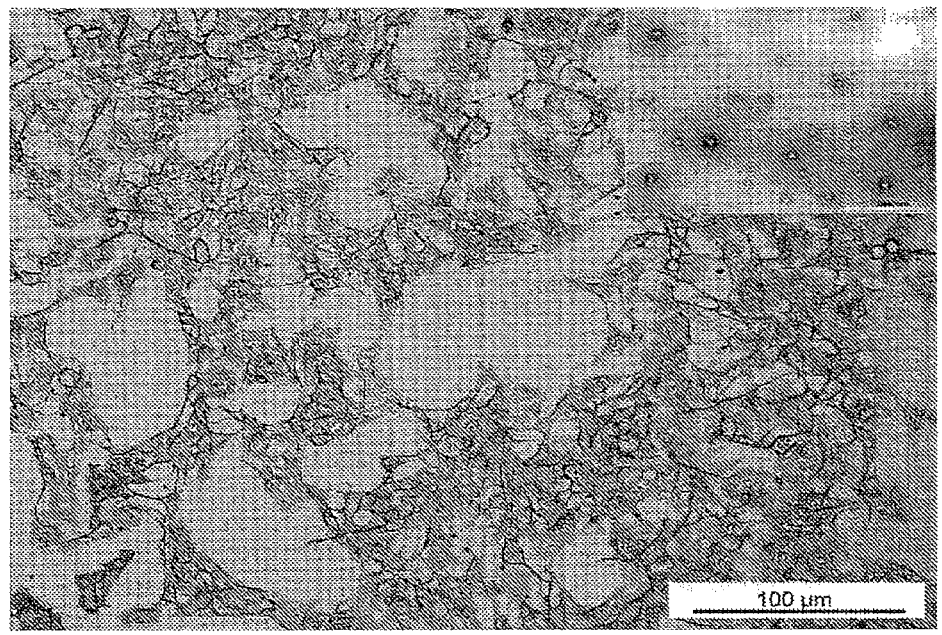
FIG. 8C shows BPLP-Ser nanoparticle-uptaken 3T3 fibroblasts observed under the light microscope (20×), scale bar is 100 μm, with an inset TEM picture of BPLP-Ser nanoparticles (80 nm)
Figure 8D:
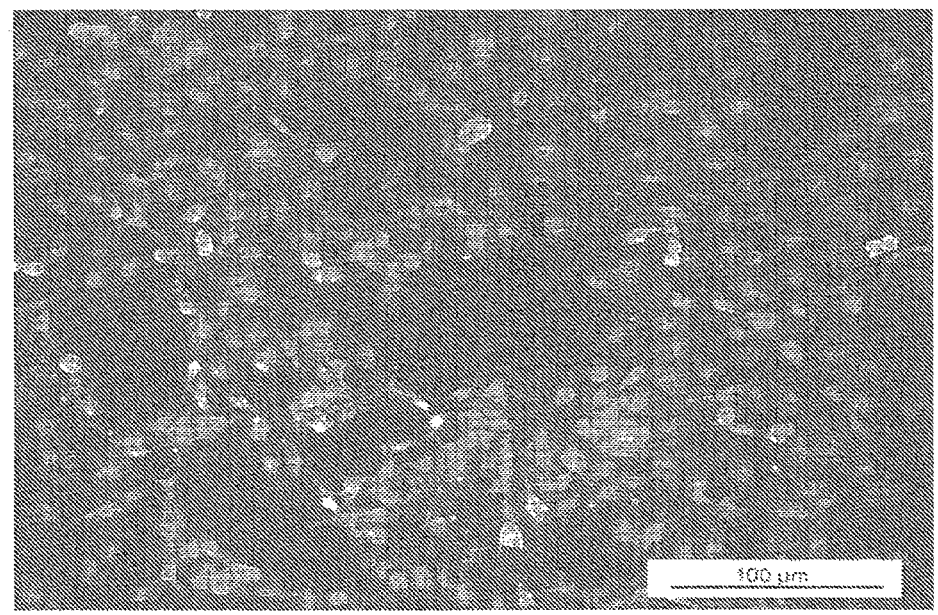
FIG. 8D shows BPLP-Ser nanoparticle-uptaken 3T3 fibroblasts observed under fluorescent microscope with FITC filter (20×), scale bar is 100 μm.
Figure 8E:
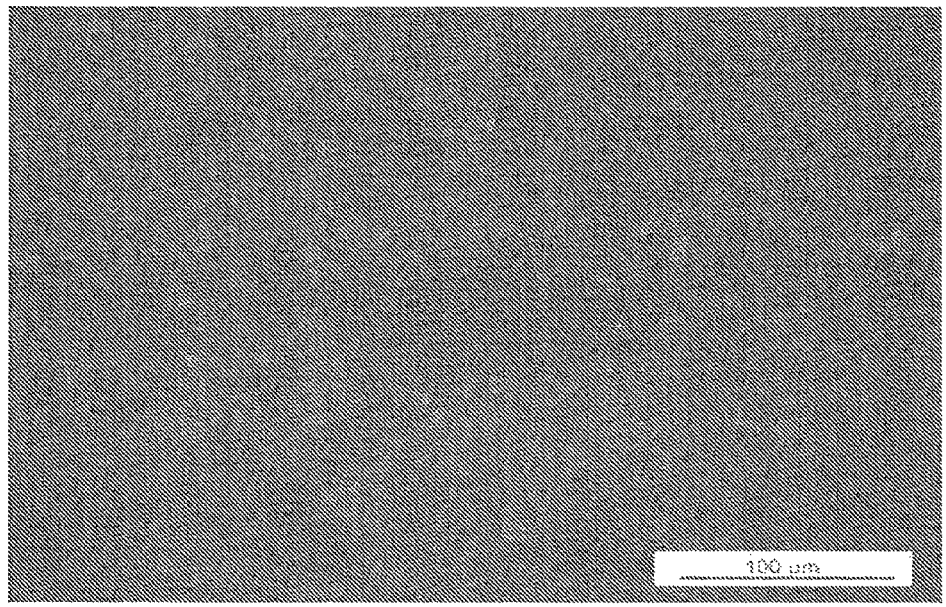
FIG. 8E shows BPLP-Ser nanoparticle-uptaken 3T3 fibroblasts observed under fluorescent microscope with Texas Red filter (20×), scale bar is 100 μm.
Figure 8F:
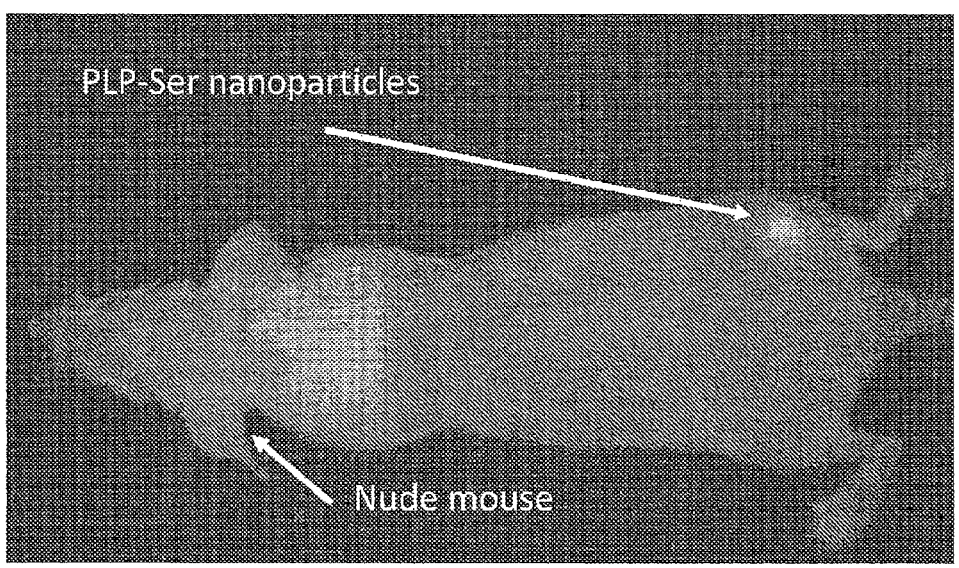
FIG. 8F shows the fluorescence image of BPLP-Ser nanoparticles injected subcutaneously in a nude mouse.
Figure 8G:
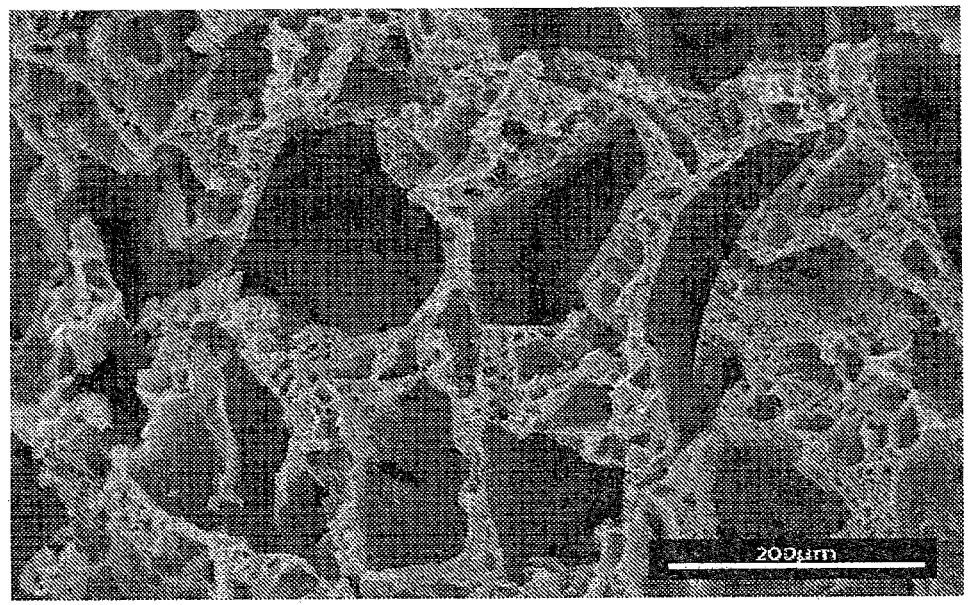
FIG. 8G shows the SEM picture of the cross section of a porous BPLP-Ser scaffold, scale bar is 200 μm.
Figure 8H:
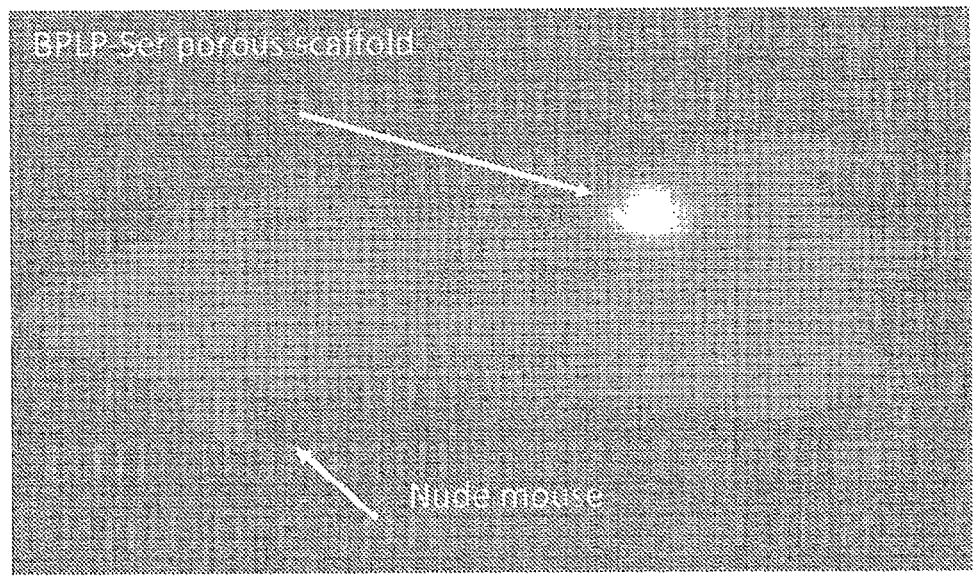
FIG. 8H shows the fluorescence image of BPLP-Ser porous scaffold implanted subcutaneously in a nude mouse.

FIGS. 7A and 7B shows the HPLC-ESI-MS analysis of soluble in vitro degradation products for BPLP-Cys and BPLP-Ser degraded in 0.05 M NaOH for 24 hours, respectively. The figures show total ion chromatograms in the negative ionization mode from HILIC mode separation of degradation products. Insets show a large amount of citric acid (192 Da) is detected as the dominant product from both polymer digests. Other signals are preliminarily attributed to soluble oligomers. Analysis of soluble in vitro degradation products (0.05 M NaOH for 24 hours) derived from BPLP-Cys and BPLP-Ser by high performance liquid chromatography—electrospray ionization—mass spectrometry (HPLC-ESI-MS) revealed the presence of a large amount of citrate, in addition to other soluble oligomers. The solution of degraded polymer, after filtering nonsoluble material, still exhibited significant fluorescence, indicating the presence of intact fluorophores in solution and their increased resistance to mild NaOH digestion. While the fluorophore remained intact, this analysis indicated that the primary degradation mechanism for the polymer in vitro is a return to monomeric material. Taken together, these studies suggest that that Pre-POC is more susceptible to degradation than BPLP-Ser or BPLP-Cys (at least that portion of the polymer which contains the appended amino acid). Still, degradation in higher concentrations of NaOH for extended periods (1 M NaOH for 48 hours) did abolish fluorescence, indicating the potential for total degradation of the polymer under appropriate conditions.

Figure 6C:
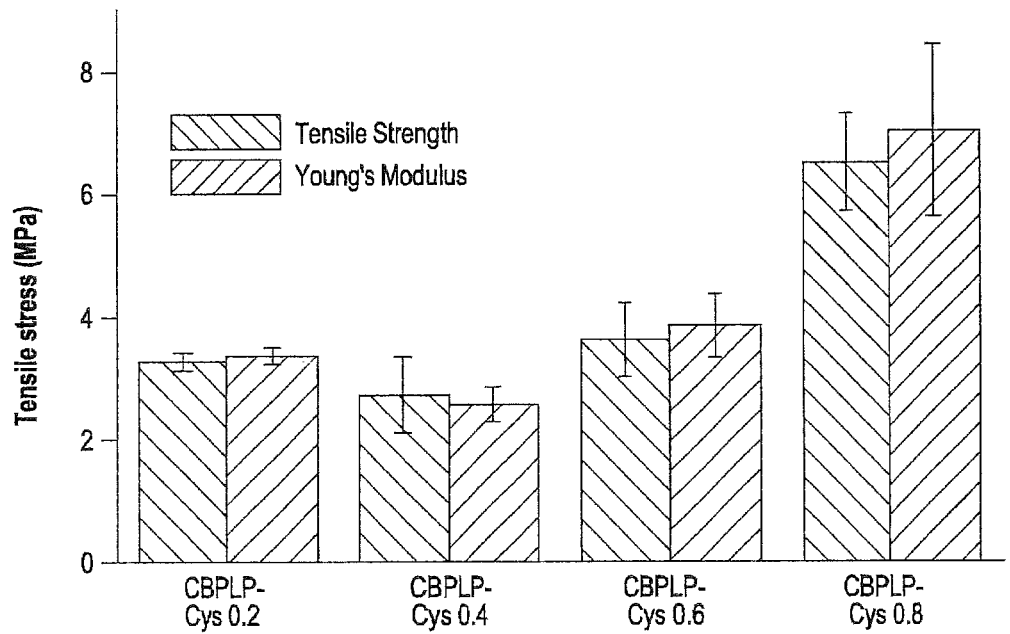
FIG. 6C shows the tensile strength and initial Young's modulus of CBPLP-Cys synthesized with various molar concentration of L-cysteine (n=5)
Figure 6D:
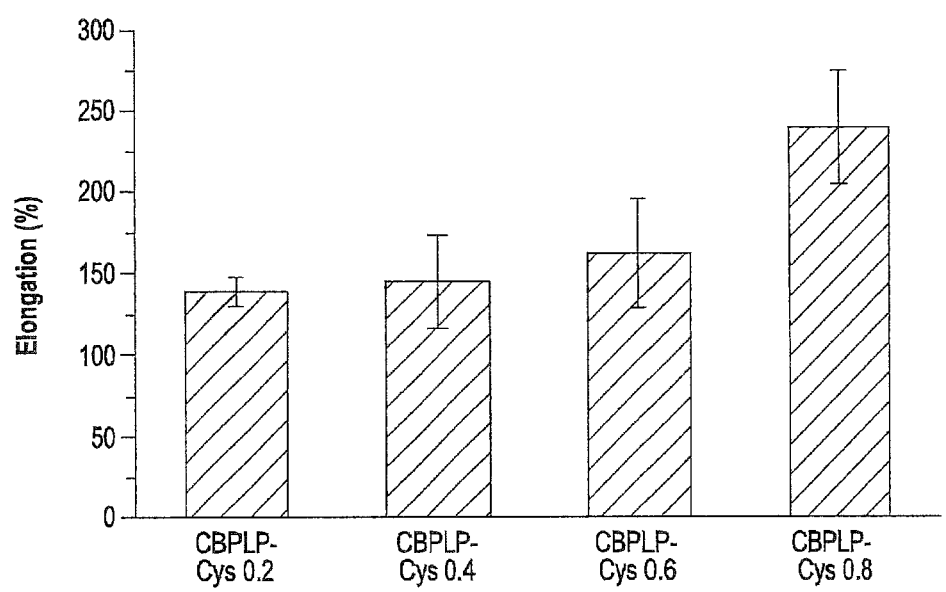
FIG. 6D shows the elongation of CBPLP-Cys synthesized with various molar concentration of L-cysteine (n=5)

The mechanical properties could be adjusted by varying ratios of monomers and by altering polymerization conditions. As shown in FIGS. 6C and 6D, the tensile strength for CBPLP-Cys ranged from 3.25±0.13 MPa to 6.5±0.8 MPa and the initial Modulus was in a range of 3.34±0.15 MPa to 7.02±1.40 MPa, which were stronger than those of POC elastomers.[25] CBPLP-Cys could be elongated up to 240±36%, which is comparable to reports of such values for arteries and veins.[25] The compressive modulus of BPLP-Cys (0.6) (1:1:0.6 OD:CA:Cys) scaffold was 39.60±5.90 KPa confirming the soft nature of the scaffolds, similar to that reported for soft elastomers including poly(diol citrates) (POC), poly(glycerol sebacate) and xylitol-based polymers.[25, 27-30]

Cytotoxicity Evaluation and Bioimaging Study In Vitro and In Vivo:

Cyto-compatibility of BPLPs and CBPLPs and their potential applications for cellular bioimaging, drug delivery, and tissue engineering were evaluated (FIG. 8). CBPLP-Cys films were found to support 3T3 mouse fibroblast adhesion and proliferation. Viable cell numbers on CBPLPs were significantly higher than those on controls POC film and poly(D,L-lactide-co-glycolide) (PLGA 75/25) film at day 7 ($P<0.05$) (FIG. 8A). Importantly, cytotoxicity evaluation for degradation products suggested that the degradation of BPLPs and CBPLPs generated similar cytotoxicity to the controls POC and PLGA75/25 ($P>0.05$) (FIG. 8B). When implanted in vivo, the CBPLP-Ser scaffolds did not trigger noticeable edema and tissue necrosis on the tested animals. Samples that were implanted for 5 months produced a thin fibrous capsule, characteristic of a weak chronic inflammatory response (FIG. 9), which was expected and consistent with the introduction of foreign materials into the body. When implanted in vivo, the polymer scaffolds did not trigger edema and tissue necrosis on the tested animals. Samples that were implanted for 5 months produced a thin fibrous capsule, characteristic of a weak chronic inflammatory response, which was expected and consistent with the introduction of foreign materials into body Intake of BPLP-Ser nanoparticles by cells generated cells labeled with various fluorescence colors (FIGS. 8C to 8E). Following subcutaneous implantation in nude mice, BPLP-Ser nanoparticles and CBPLP-Ser scaffolds (FIG. 8G) were readily detected in vivo using a non-invasive imaging system (FIGS. 8F and 8H).

The potential future applications of the unique BPLP families are worthy of further note. BPLPs can be used as fluorescence probes offering advantages over the traditional organic dyes and semiconductor quantum dots due to their tunable fluorescence emission, high quantum yield, degradability, photostability, and cell compatibility. The inventors have shown in the present disclosure that BPLP nanoparticles ("biodegradable quantum dots") can be used to label cells. Thus, it may be possible to develop a biodegradable fluorescent drug delivery system using BPLPs avoiding the long-term toxicity associated with current labels. The low molecular weight BPLPs can be made to be water-insoluble or -soluble maximizing their potential applications in biological labeling and imaging. The water soluble low-molecular-weight BPLPs may potentially be used for single molecule labeling such as protein and DNA labeling in proteomics and genomics research, where quantum dots may not be ideal due to their size.[7, 8] The BPLP family may also be suitable for use in fluorescence resonance energy transfer (FRET),[5] two-photon excited fluorescence microscopy,[6] multimodal compositions (combined with magnetic or radionuclear agents),[31] and biosensors.[32] BPLP polymers provide real promise for non-invasive real-time monitoring of the scaffold degradation and tissue infiltration/formation in vivo, which has been a challenge in the evolving field of tissue engineenng.[33-35] The results obtained by the inventors have demonstrated that the fluorescent BPLP nanoparticles and CBPLP scaffolds could be imaged in vivo with negligible interference from tissue autofluorescence. In addition the in vivo scaffold bioimaging will open new avenues for soft tissue engineering studies and may provide an opportunity for doctors to track clinical outcomes without an open surgery.

Figure 10A:
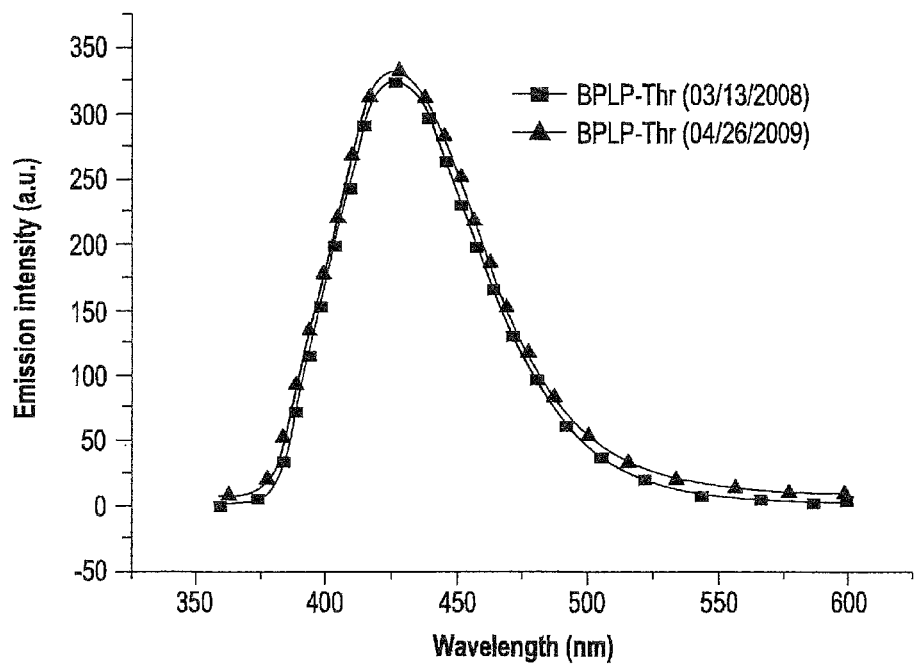
FIG. 10A shows photoluminescent properties of BPLP-Thr0.2 stored in amber glass bottles at −20° C. for over a year.
Figure 10B:
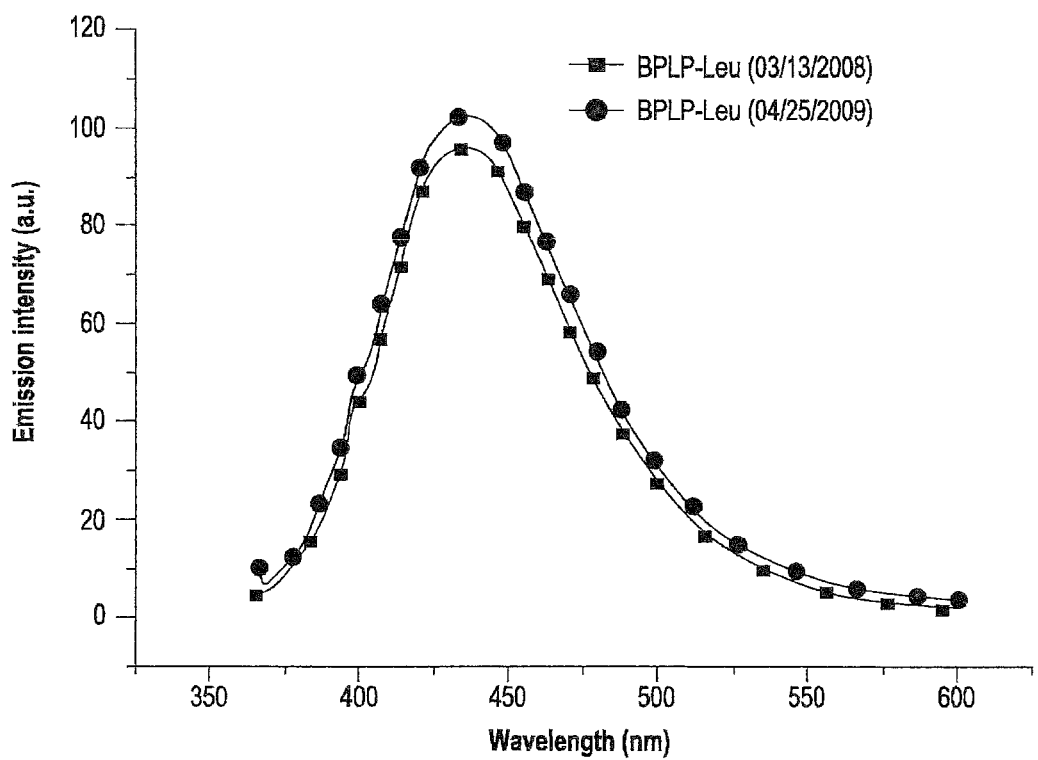
FIG. 10B shows photoluminescent properties of BPLP-Leu0.2 stored in amber glass bottles at −20° C. for over a year.

Synthesis and Characterization of BPLPs and CBPLPs:

For BPLP synthesis, equimolar amounts of citric acid and 1,8-octanediol were combined and stirred with additional L-cysteine at molar ratios of L-cysteine/citric acid 0.2, 0.4, 0.6, and 0.8. After melting the mixture at 160° C. for 20 minutes, the temperature was brought down to 140° C. stirring continuously for another 75 minutes to obtain the BPLP-cysteine (BPLP-Cys) oligomers or low-molecular-weight compounds. The oligomers were purified by precipitating the oligomer/1,4-dioxane solution in water followed by freeze drying. Each of the 20 (L-) amino acids was used to synthesize a family of BPLP-amino acid polymers. Water soluble polymer (BPLP-PEG-amino acid) was synthesized using poly (ethylene glycol) (PEG), citric acid, and amino acid. Other aliphatic diols ($C_3$-$C_{12}$ diols) can also be used for BPLP synthesis similar to our previously developed poly (diol citrates).[24] The synthesized BPLPs have a shelf-life of over a year without significant changes on their photoluminescent properties (emission wavelength and intensity) when stored in amber glass bottles at −20° C. (FIG. 10). The results of the storage stability evaluation indicates that BPLPs has shelf-life of at least a year in terms of its photoluminescent properties when stored in amber glass bottles at −20° C.

For CBPLP film synthesis, BPLP was dissolved in 1,4-dioxane to form a 30 wt. % solution and then cast into a Teflon mold followed by solvent evaporation and then post-polymerization at 80° C. for 4 days. For CBPLP scaffold fabrication, a common salt-leaching method was applied.[36] For BPLP nanoparticle preparation, 0.6 g of BPLP was dissolved in acetone (10 ml). The polymeric solution was added dropwise to deionized water (30 ml) under magnetic stirring (400 rpm). The setup was left overnight in a chemical hood to evaporate the acetone. TEM (JEOL-1200 EX II) and dynamic light scattering (DLS, Microtrack) were used to determine the size, shape, and size distribution of the nanoparticles. The BPLPs were characterized by Fourier Transform Infrared (FT-IR), $^1$H- and $^{13}$C-nuclear magnetic resonance (NMR), and matrix-assisted laser desorption/ionization mass spectroscopy (MALDI-MS; Bruker Autoflex).

Photoluminescent Properties:

Photoluminescence spectra of BPLP-Cys0.2 solutions and nanoparticles, and CBPLP-Cys0.2 films and scaffolds were acquired on a Shimadzu RF-5301 PC fluorospectrophotometer. Both the excitation and the emission slit widths were set at 1.5 nm for all samples unless otherwise stated. The Williams' method was used to measure the fluorescent quantum yield of the BPLP polymers.[37] The photostability of BPLP-Cys solution, BPLP-Cys film, BPLP-Ser solution, and Rhodamine B solution were evaluated by recording the changes of the fluorescence intensity of the samples under continuous excitation in the fluorospectrophotometer. The excitation wavelength for photostability tests was determined by the maximum absorbance spectra of each type of sample. The fluorescence changes with degradation were determined by measuring the fluorescence intensity of the solutions of BPLP-Cys degraded in 0.05 M NaOH under 37° C. at various degradation degrees and at the same concentration.

Mechanical Tests and Degradation Studies:

The tensile mechanical tests on CBPLP films were conducted according to ASTM D412a on a MTS Insight 2 mechanical tester.[24] The initial modulus was measured from a slope of stress-strain curve at 10% of strain. The compressive tests on CBPLP scaffold (90% porosity, 100 μm pore size, 3 mm height, 6 mm diameter) were conducted according to a method described previously.[30] The in vitro degradation of BPLP and CBPLP polymers were conducted by incubating the polymers in phosphate buffered saline (pH=7.4) at 37° C. for various times to obtain polymer mass loss.[36] To analyze the degradation products of the BPLPs, three grams of BPLPs were degraded in 0.05 M NaOH for 24 hour and in 1 M NaOH for 48 hours. Soluble degradation products were investigated by high performance liquid chromatography—electrospray ionization—mass spectrometry (HPLC-ESI-MS; Shimadzu LCMS-2010), using hydrophilic interaction chromatography (HILIC) on an amide-bonded stationary phase (Tosoh Bioscience Amide-80). The filtered (0.2 μm PTFE syringe filter; Whatman), in vitro degraded sample of BPLP-Cys was analyzed to track the presence of monomers based on retention time and mass-to-charge ratio (matched to the analysis of standards) in the negative ionization mode.

Cytotoxicity Evaluation:

Mouse 3T3 fibroblasts were used to evaluate the cytocompatibility of the polymers. The cell viability and proliferation on CBPLP-Cys0.2 and CBPLP-Ser0.2 films (80° C., 4 d) was determined by Methylthiazoletetrazolium (MTT) assay as described previously.[36] The cell morphology was observed under scanning electron microscopy (SEM, Hitachi 3500N). Cytotoxicity of the polymer degradation products was investigated according to a method described elsewhere.[38] Briefly, BPLP-Cys, BPLP-Ser and their CBPLPs (80° C., 4 days) were hydrolytically degraded in 1M NaOH solution at 37° C. over a period of 24 h to 72 h. The solution was then filtered through a cellulose acetate membrane syringe filter (0.2 μm pore diameter). The pH was adjusted to 7.4 with 1 M HCl. The solution was filtered again for sterilization and then diluted by 2, 10, 50 and 100 times with culture medium. The solutions were added to the cultured cells (n=5 wells for each polymer dilution) in 96 well plates (100 μl/well) and incubated at 37° C. and 5% $CO_2$ for 24 h. Cell viability was then determined using MTT assay. POC (80° C., 4 d) and poly(D,L-lactide-co-glycide) (PLGA75/25, Mw=113 KDa, Lakeshore Biomaterials, Birmingham, Ala.) were used as controls for the above cytotoxicity evaluation. The statistical significance between two sets of data was calculated using a Student's t test. Data were considered to be significant when a p value of 0.05 or less was obtained (showing a 95% confidence limit).

Bioimaging Studies In Vitro and In Vivo:

For cellular fluorescence-labeling in vitro, 3T3 mouse fibroblasts were seeded on sterile glass cover slips at a density of 5000 cells/ml for 24 h prior to the cellular uptake study. The cover slips were washed with PBS and transferred to new Petri dishes, and then incubated with a BPLP-Ser0.2 nanoparticle solution in PBS (2% wt, 80 nm in diameter) for 4 hours at 37° C. At the end of the study, the cells were washed (PBS×3) and then fixed with glutaraldehyde solution (2.5%). Cells were observed under a Leica DMLP microscope (Nikon Corp. Japan). For nanoparticle/scaffold bioimaging in vivo, BPLP-Ser0.2 nanoparticles (2% wt in PBS, 80 nm in diameter, sterilized by filtering through a syringe filter (0.22 μm)) and CBPLP-Ser0.2 scaffolds (6 mm in diameter, 90% porosity, 100 μm pore size, 1.5 mm thick, sterilized by 70% ethanol and UV light) were injected/implanted subcutaneously in nude mice (BALB/c nu/nu). The mice were then imaged using a CRi Maestro Imaging System, as described previously,[14, 39] immediately after the implantation. CBPLP-Ser scaffolds subcutaneously implanted in nude mice for 5 months (n=4) were sectioned for hematoxylin and eosin (H&E) staining to preliminarily evaluate the long-term in vivo host responses to the polymers.

To non-invasively monitor the scaffold degradation in vivo, it is imperative to understand the relation of scaffold fluorescence properties and the scaffold degradation over time in vitro. The fluorescence of polymers is proportional to the concentration of the polymers. The scaffold degradation may cause the changes of fluorescence intensity, wavelength, and size of fluorescent scaffold. Therefore, the present inventors established a novel non-invasive fluorescence based bioimaging method to study the scaffold degradation and tissue/scaffold interaction in vitro and in vivo using a cutting-edge CRI Maestro Fluorescence Imaging system.

Figure 11:
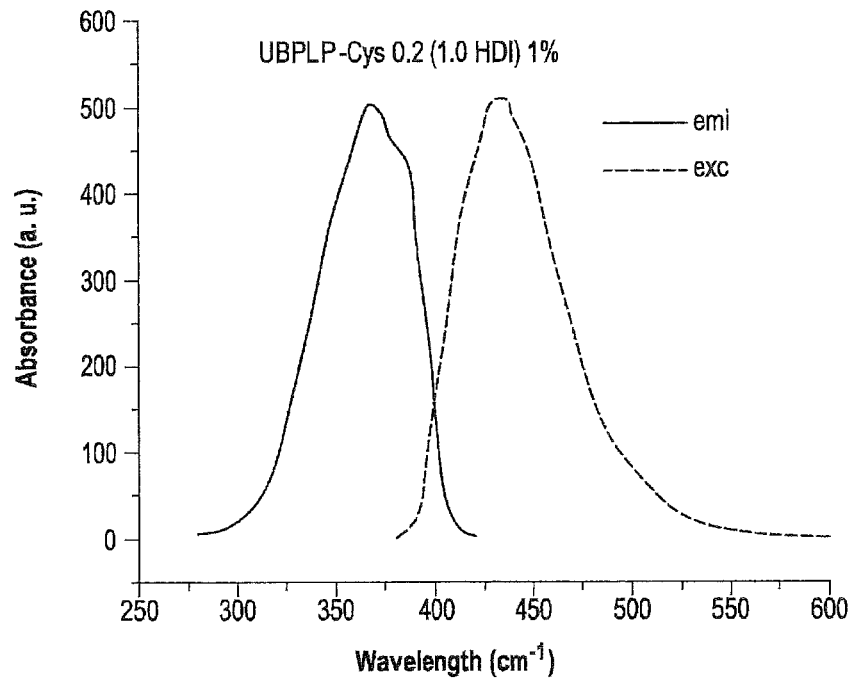
FIG. 11 shows the excitation and emission spectra of UBPLP-Cys.
Figure 12:
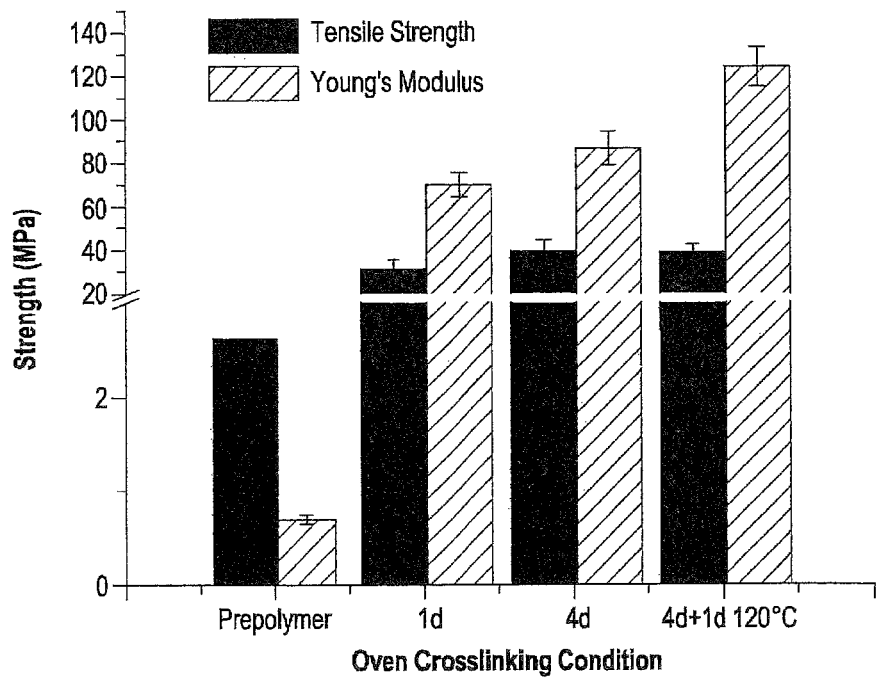
FIG. 12 shows the tensile strength and initial Young's modulus of CUBPLP-Cys0.2 with different thermo-crosslinking condition.
Figure 13:
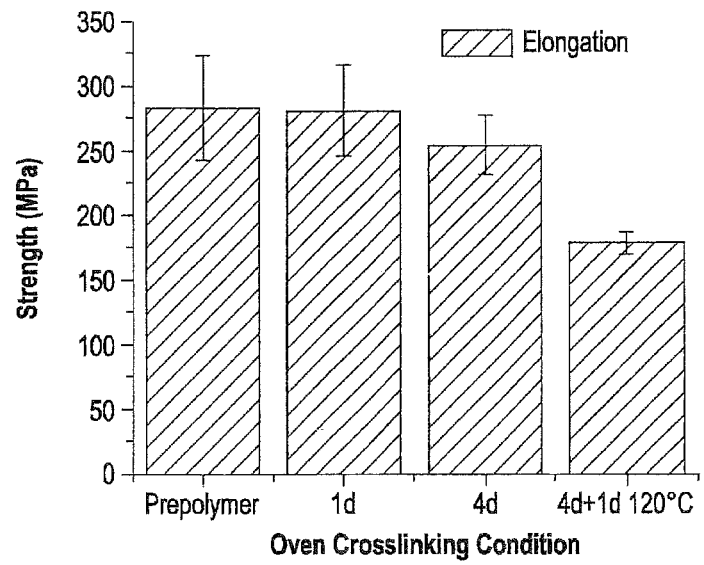
FIG. 13 shows the elongation of CUBPLP-Cys0.2 with different thermo-crosslinking condition.

The present inventors have also devised methods for synthesizing crosslinked urethane-doped BPLP (CUBPLP), water-soluble BPLP (WBPLP), and photo-crosslinkable BPLP (PCBPLP). The methods of synthesis and characteristics of the BPLP variants is described below:

Crosslinked Urethane-Doped BPLP (CUBPLP):

CUBPLP synthesis was carried out in three steps. Step 1, citric acid and 1,8-octanediol, with a monomer ratio of 1:1.1, were bulk polymerized in a round bottom reaction flask. After the monomers had melted at 160° C., the temperature was lowered to 140° C., and the reaction mixture was stirred for another 20 minutes to create the oligomer of poly (octamethylene citrate). Then additional L-cysteine at molar ratios of L-cysteine/citric acid 0.2, 0.4, 0.6, and 0.8 was added into the mixture and stirred for another 60 minutes. The pre-BPLP-Cys was purified by drop wise precipitation in deionized water. Undissolved pre-BPLP-Cys was collected and lyophilized to obtain the purified BPLP prepolymer. The average molecular weight of pre-BPLP-Cys was characterized as 1300 Da by Matrix assisted laser desorption/ionization mass spectroscopy (MALDI-MS) using an Autoflex MALDI-TOF Mass Spectrometer (Bruker Daltonics, Manning Park, Mass.). Chain extension of the BPLP pre-polymer to obtain pre-CUBPLP was done in step 2. Purified pre-BPLP-Cys was dissolved in 1,4-dioxane to form a 3% (wt/wt) solution. The polymer solution was reacted with 1,6-hexamethyl diisocyanate (HDI) in a clean reaction flask under constant stirring, with stannous octoate as catalyst (0.1% wt). Different pre-CUBPLP polymers were synthesized with different feeding ratio of pre-BPLP:HDI (1:0.5, 1:1.0, and 1:1.5, molar ratio) and different amino acids. The system was maintained at 55° C. throughout the course of the reaction. Small amounts of the reaction mixture were removed at 6 hour intervals and subjected to Fourier transform infrared (FT-IR) analysis. The reaction was terminated when the isocyanate peak at 2267 $cm^{-1}$ disappeared. In step 3, the pre-CUBPLP (UBPLP) solution was cast into a laminar airflow until all the solvents had evaporated. The resulting UBPLP film was moved into an oven maintained at 80° C. for pre-determined time periods to obtain crosslinked urethane-doped polyester (CUBPLP). The excitation and the emission spectra of the synthesized UBPLP-Cys are shown in FIG. 11. The quantum yield of UBPLP-Cys0.2 was 36%. The tensile strength of CBPLP-Cys0.2 was as high as 40 MPa with 275% elongation (FIGS. 12 and 13).

Figure 14:
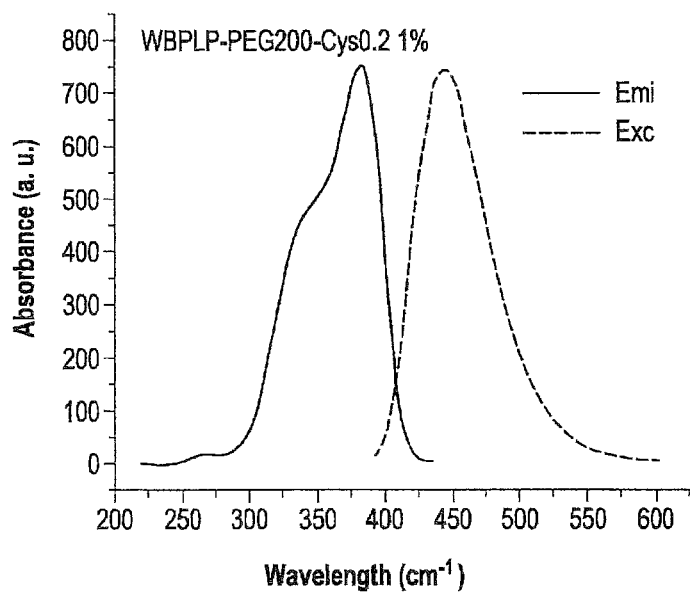
FIG. 14 shows the excitation and emission spectra of WBPLP-PEG200-Cys0.2.
Figure 15:
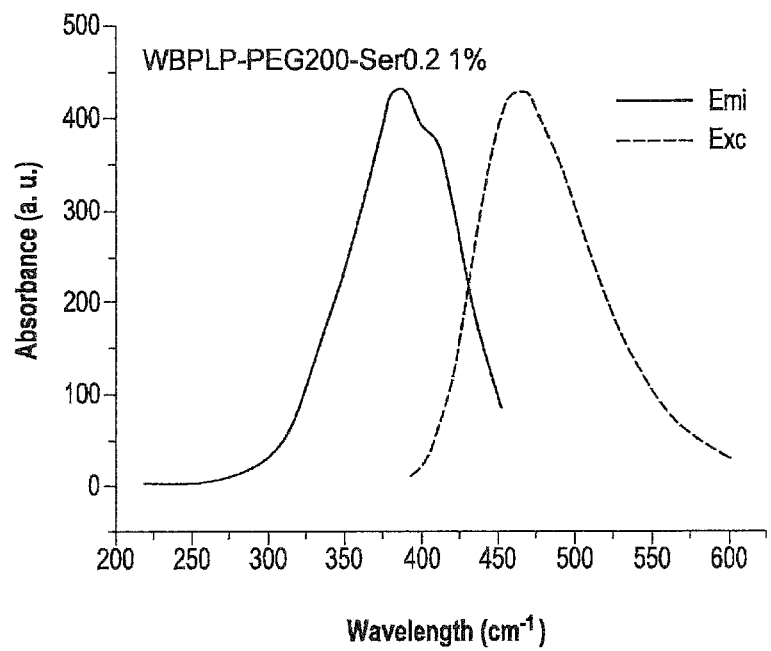
FIG. 15 shows the excitation and emission spectra of WBPLP-PEG200-Ser0.2.
Figure 16:
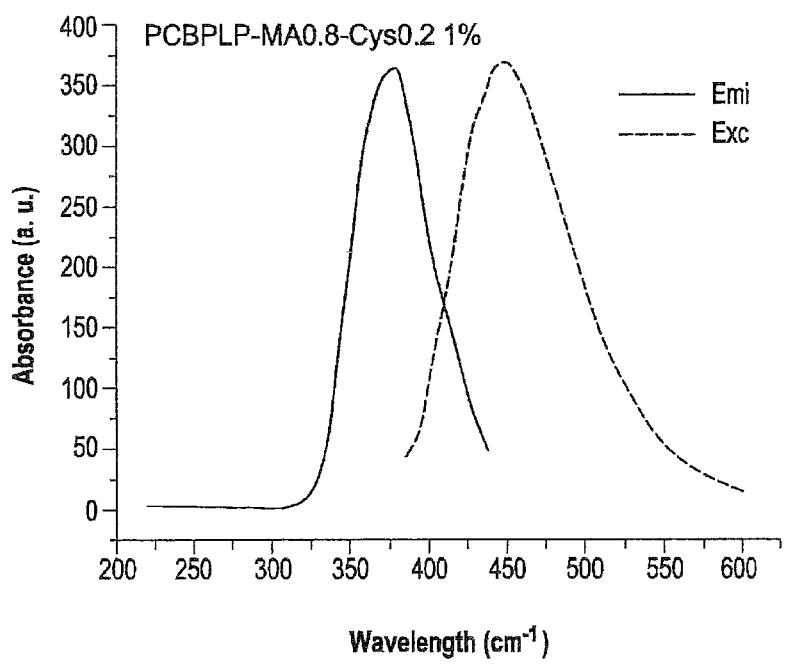
FIG. 16 shows the excitation and emission spectra of PCBPLP-MA0.8-Cys0.2.

Water-Soluble BPLP (WBPLP):

For Water-soluble BPLP (WBPLP) synthesis, citric acid and poly(ethylene glycol) at molar ratio of 1:1.1 were combined and stirred with additional L-cysteine at molar ratios of L-cysteine/citric acid 0.2, 0.4, 0.6, and 0.8. After melting the mixture at 160° C. for 30 minutes, the temperature was brought down to 140° C. stirring continuously for another 8 h to obtain the WBPLP-cysteine (WBPLP-Cys) linear prepolymer. The prepolymers were purified by dialysis against deionized water using dialysis bag with molecular weight cut off of 500 Da. The DI water was changed every 6 hours. After one week, the polymer solution was freeze dried. Each of the 20 (L-) amino acid was used to synthesize a family of WBPLP-amino acid polymers. The quantum yields of WBPLP-Cys0.2 and WBPLP-Ser0.2 were 40% and 22% respectively. The excitation and emission spectra of WBPLP-PEG200-Cys0.2 and WBPLP-PEG200-Ser0.2 are shown in FIGS. 14 and 15 respectively, Photo-Crosslinkable BPLP (PCBPLP):

The Photo-crosslinkable BPLP was synthesized as following steps. First, citric acid, maleic acid, and 1,8-octanediol were added into a round bottom reaction flask with molar ratio of 0.2:0.8:1.1. The mixture was melted under 160° C. Additional amount of L-Cysteine with molar ratios of L-cysteine/acid 0.2, 0.4, 0.6, and 0.8 was added into reaction system and stirred continuously for another 6 hours to obtain the PCBPLP-cysteine. The PCBPLP-cysteine was purified by drop wise precipitation in deionized water. After purification, the prepolymer was then lyophilized for further characterization. FIG. 16 shows the excitation and emission spectra of PCBPLP-MA0.8-Cys0.2. The family of PCBPLP was obtained by using 20 (L-) amino acid for synthesis.

Figure 17A:
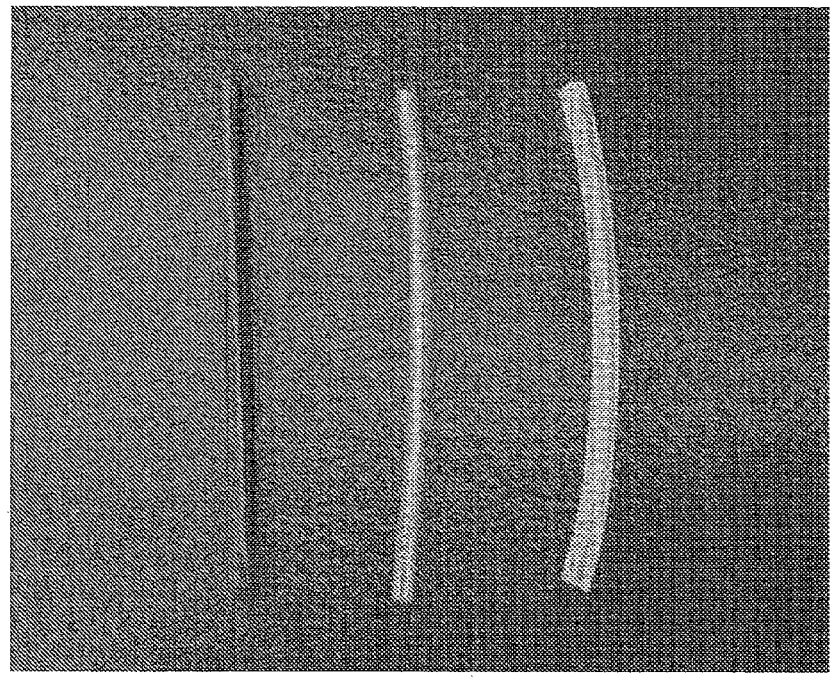
FIG. 17A shows the tubes fabricated from the BPLP of the present invention under natural light.
Figure 17B:
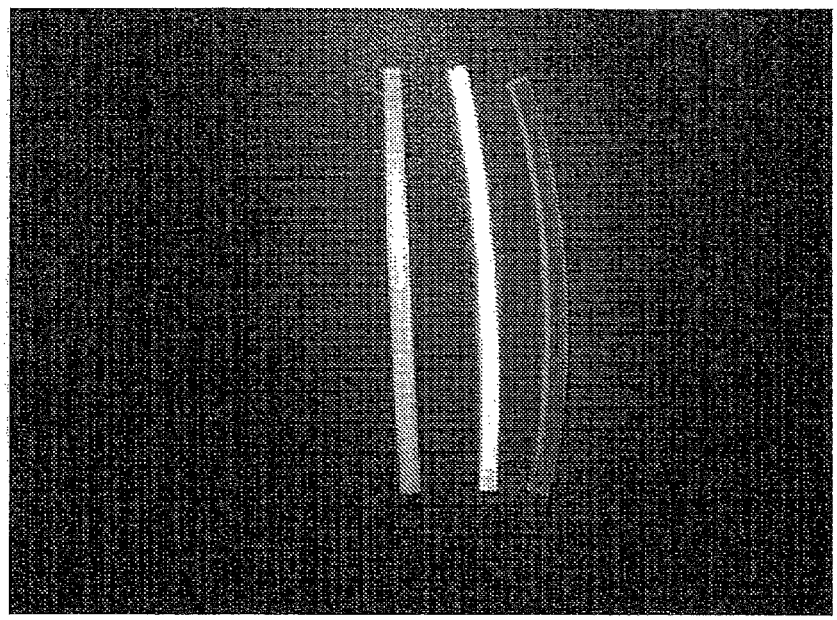
FIG. 17B shows the tubes fabricated from the BPLP of the present invention under UV light.

The present inventors also fabricated tubes and soft and elastic CBPLP SDBV scaffolds via a scaffold-sheet tissue engineering strategy. FIGS. 17A and 17B shows the tubes fabricated from the BPLP of the present invention under natural light and UV light, respectively. In order to assess whether the CBPLP scaffold-sheet SDBV graft design can modulate cell-cell communication, cell proliferation, cell differentiation, cell migration and matrix production for SDBV regeneration was studied in an in vitro in a perfusion bioreactor via histological analysis and bioimaging tool.

The feasibility of growing small diameter blood vessels (SDBV) in vitro in a bioreactor using cell-seeded CBPLP grafts was studied. The anatomy of artery shows that the elastic lamina separates the endothelium and the medium layer (smooth muscle cell (SMC) layer) surrounded by adventitial layer (fibroblasts). In vivo, each cell types of the vascular wall is "dependent" on its neighboring cells, and all act synergistically toward the development, maintenance, remodeling, and regulation of the tissue under physiological and pathological conditions. Interaction between endothelial cells (ECs) and SMCs was believed to be important in determining vessel diameter, thickness, SMC proliferation and phenotype via either physical contact or their secreted soluble biological mediators such as transforming growth factor-1 (TGF-1).[42] Many studies have focused on the SMC-EC communications. However, the fibroblast cell seeding was not included due to the incapability of seeding the third cell types in those scaffold designs.[43-48] There was no any scaffold design that could address all the concerns of the compartmentalization of the three types of cells (fibroblasts, SMCs and ECs) without hampering the cell-cell communication between SMCs and ECs, the uneven cell distribution, the compliance mismatch, and the off-the-shelf availability for in vivo tissue engineering SDBVs. The inventors assessed whether the CBPLP scaffold-sheet graft can serve as a model to study the SMC-EC communications in existence of fibroblasts, cell migration, differentiation and matrix production in vitro via a perfusion bioreactor. The fluorescent CBPLP SDBV grafts were also characterized by the Maestro Imaging System to monitor the scaffold degradation and tissue regeneration.

Scaffold-Sheet Fabrication:

As previously shown by the inventors the poly(ethylene glycol) dimethyl ether (PEGDM) can be used as a porogen to create tortuous nano- or sub-micro channels in the POC films,[49] a permeable CBPLP-ser tube (50-100 μm of thickness, 3 mm in diameter) was fabricated by dip-coating a glass rod (3 mm in diameter) into the BPLP/PEGDM (Mw=400, 20 wt % of BPLP-ser) solution followed by solvent evaporation, postpolymerization, PEGDM leaching, and then freeze-drying.

The permeability of the tubes was tested according to the method described previously.[50] Thin CBPLP porous scaffold sheets (100 μm thick, 100 μm of pore size) were fabricated via a thermally inductive phase separation method by freeze-drying BPLP-ser solution in a teflon mold followed by post-polymerization in an oven (80° C., 4 days). The macropore structure and nanoporous features of CBPLP-ser scaffold and lumen tubes were observed by high resolution SEM.

Figure 18:
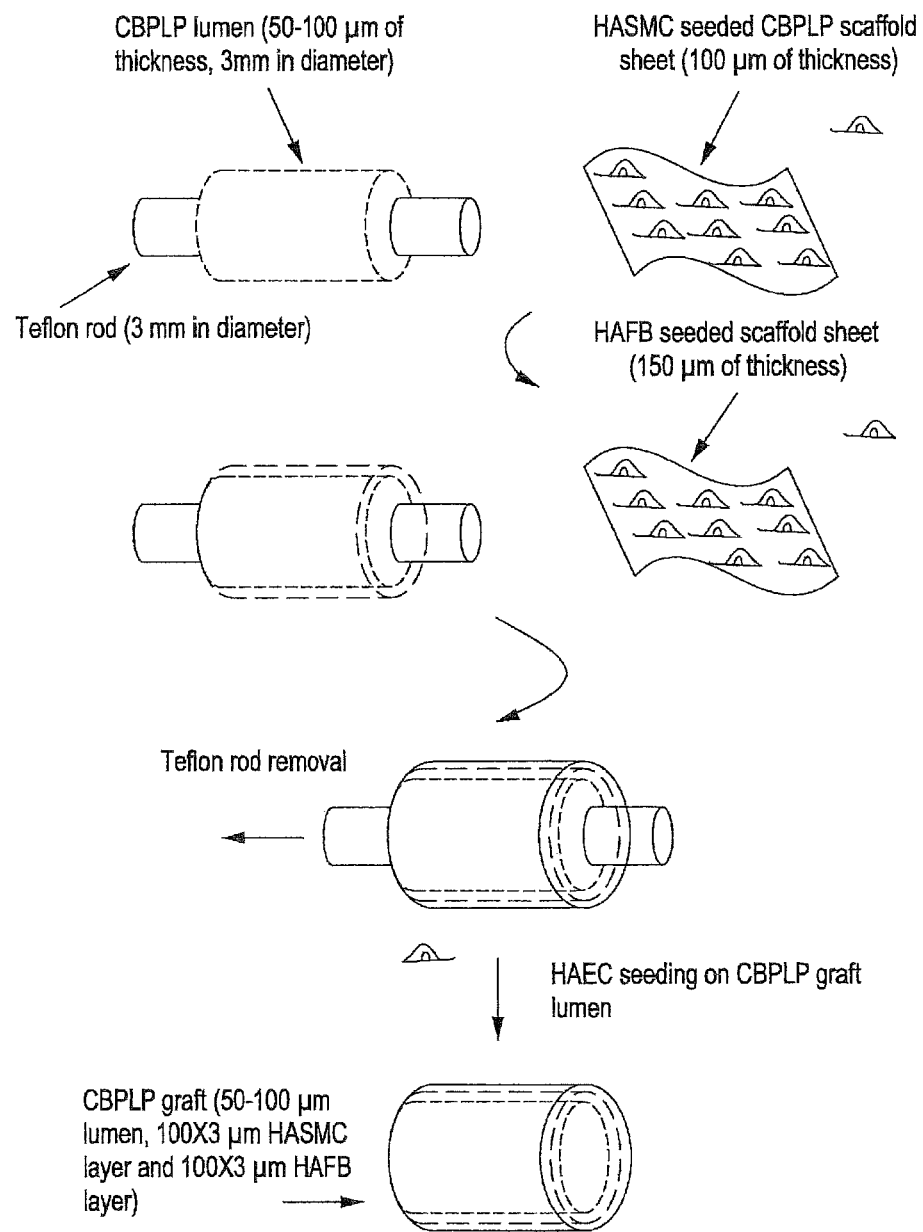
FIG. 18 is a schematic representation of BPLP scaffold-sheet strategy for blood vessel tissue engineering.

Construction of SDBV Graft Using Cell-Seeded Fluorescent CBPLP-Ser Scaffold Sheets:

6 CBPLP-ser scaffold sheets and one permeable CBPLP-ser tube were used for cell seeding and fabrication of the tubular SDBV graft (FIG. 18). Scaffold sheet 1-3 was be seeded with human aortic fibroblasts (HAFBs) by pipetting $5 \times 10^6$ cells/ml of HAFBs evenly into the scaffold; Scaffold sheet 4-6 were seeded with human aortic smooth muscle cells (HASMCs) by pipetting $5 \times 10^6$ cells/ml of HASMCs evenly into the scaffold. After 2 days of in vitro culture, a CBPLP SDBV graft was constructed by rolling HASMCs seeded CBPLP-ser sheets and HAFBs seeded CBPLP-ser sheets on a permeable CBPLP-ser tube sequentially on the Teflon rod (3 mm in diameter). After the rod removal, then human aortic endothelial cells (HAECs) with a density of $1 \times 10^6$ cells/ml were seeded on the lumen of the tubular graft according a method described previously.[29] The resulting cell-seeded CBPLP graft will be further cultured in vitro for 3 days in a coculture medium[45] for further bonding between the layers of the graft before it is assembled in a perfusion bioreactor.

Tissue Culture in a Perfusion System:

A custom-made perfusion bioreactor chamber was assembled into a similar close-loop flow system.[51] A LED micrometer (Keyence LS7000) was used to non-invasively measure radial distension imparted to the engineered vessels. The pressure and distension data over time were recorded with LabVIEW software (National Instruments, Austin Tex.). Percent distention was calculated from the maximum and minimum diameters [((Dmax−Dmin)/Dmin)×100]. Blood vessel graft compliance was be obtained by dividing the % distention by the measured pressure.

The whole system was set up in a standard cell culture incubator. Two CBPLP grafts were assembled in one bioreactor chamber. Three bioreactor chambers were juxtaposed into the close-loop system for the following studies. CBPLP grafts were constructed as described above. Two grafts per chamber were mounted on the hollow posts. For cell-cell communication study, 6 fully seeded grafts with permeable lumen tube (fibroblasts, SMCs and ECs), 6 partially seeded CBPLP graft with permeable lumen tube (SMCs and ECs), and 6 fully seeded CPEU grafts with non-permeable lumen tube (without using PDMEG as nanoporogen) were used. The cell culture medium flow was kept at 40 ml/min and at a pulse frequency of 1.5 Hz by the peristaltic pump.[45, 52] The above three types of grafts were simultaneously cultured for 3 days, 15 days, 28 days, respectively (2 grafts per time points for each type of graft). The compliance changes over time of the CBPLP grafts were monitored at the above 3 time points to determine whether the grafts can maintain the compliance during the matrix productions before the grafts are harvested for the following characterizations. The tissue constructs were harvested from the bioreactor and imaged and characterized by the CRI Maestro Imaging system. The grafts were sectioned for biological analysis to study the matrix. production (total collagen assay,[53] elastin assay, sulfated glycosaminoglycan assay[54]); matrix distribution and cell differentiation status (H&E staining for overall cell and matrix distribution, Masson's trichrome staining for collagen, Verhoff's staining for elastin, calponin, actin, myosin heavy chain staining for human aortic smooth muscle cells (HASMC) differentiation, and vWF and VE-cadherin for human aortic endothelial cell (HAEC) differentiation).[29,30, 55, 56] SEM observation was performed on the lumen to assess the EC alignment. EC retention under the shear stress was also assessed. The non-cell-seeded (dry) and cell-seeded (wet) CBPLP grafts were subjected to the following characterization: Burst pressure,[30] and Suture retention.[57, 58] Quantitative data was analyzed using GraphPad Prism (4.0) with one-way analysis of variance or two-tail Student's t-test. Data was taken to be significant when a P value of 0.05 or less is obtained.

The present inventors have developed a convenient fluorometric method for accurate polyquaternium-1 determination using strong fluorescence-shining polymers. Polyquaternium-1 is an antibacterial preservative in pharmaceutical formulations. Therefore, the accurate determination of polyquaternium-1 is a key for quality control of products and is also vital to be able to pass the Food and Drug Administration (FDA) regulatory scrutiny.

Figure 19:
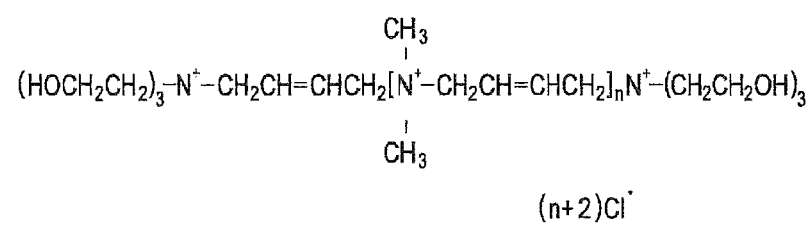
FIG. 19 shows a chemical structure of Polyquaternium-1.

Polyquaternium-1,ω-{4-[tris(2-hydroxyethyl)ammonio]-but-2-enylpoly(dimethylammoniobut-2enyl)}tris(2-hydroxyethyl)ammonium polychloride as shown in FIG. 19, is a cationic polymer with molecular weight ranging from 5,000 to 10,000. Polyquaternium-1 does not have a chromophore that absorbs above 200 nm. Therefore, polyquaternium-1, by itself, cannot be detected by spectrophotometry. The theory behind the spectrophotometric determination was that an anionic organic dye, trypan blue form a water-soluble ion pair with cationic polyquaternium-1. The formation of the water-soluble complex between polyquaternium-1 and trypan blue increases the electron delocalisation in trypan blue and produce a bathochromic shift of trypan blue absorbance from 658 to 700 nm. Thus, the absorbance of the complex can be measured at its maximum difference ($\Delta A$) from a blank at 680 nm.

The introduction of trypan blue brings a chromophore kelated with polyquaternium-1 thus provide a solution to detect the quaternium spectrophotometrically. However, there are some drawbacks which bring about the concerns on the sensitivity of the determination. Although this method measures the absorbance at the wavelength (680 nm) of maximum difference between the water soluble complex and trypan blue, the interference of background signal from trypan blue is inevitable since trypan blue also absorbs at 680 nm significantly. The absorbance for analytes may be very low, especially when the concentration of samples is low (10 ppm for polyquaternium-1) plus the background signals need to be subtracted. Thus the sensitivity of the measurement will be affected. In addition, the absorbance of samples is also affected by the pH value and ionic strength of sample solution which brings more variables to the measurements. These are intrinsic problems of absorbance measurement. The complex can be only stable for a certain period of time. Thus, the stability of the ion pairs is also a concern which may also affect the sensitivity of the determination. The low sensitivity may affect the repeatability of the absorbance measurements In conclusion, in order to detect polyquaternium-1, a chromophore (dye) can be kelated with polyquaternium-1 to confer the detectability. But the relatively strong background signal, effects of solution pH and ionic strength, stability of complex, and weak absorbance in absorbance analysis may affect the sensitivity of the determination.

The present invention describes a fluorometric method to accurately determine the concentration of polyquaternium-1. Given the fact that polyquaternium-1 is a positively charged polymer with molecular weight from 5000 to 10000, a negatively charged polymer should be able to kelate with polyquaternium-1 to form a complex. The stability of the formed ion pair complex may affect the sensitivity of the fluorometric analysis. The precursors of BPLPs are highly negatively charged polymers. The introduction of various amino acids may not only confer fluorescence to BPLP but also modulate the charge state of the polymers. Unlike trypan blue which is a small molecule and consists of mainly stiff benzene ring, the polymer backbone of BPLPs is a flexible polyester chain. The chain length of BPLP is also much longer than that of the trypan blue. It is expected that the long (around 2000 Dalton) and flexible negatively charged BPLP chains should entangle with long and positively charged polyquaternium-1 chain to form a stable ion pair complex. The entanglement should enhance the stability of the ion pair complex thus may improve the sensitivity of determination.

Fluorescence signal is proportional to the concentration of analytes. A strong fluorescence dye is preferred to detect the low concentration of analytes. Compared to the other commercially available organic fluorescence dyes, BPLPs are much stronger fluorescent polymers which amplify the signals thus improve the sensitivity of determination.

BPLPs consist of water-soluble and solvent soluble polymers. Both types of BPLP polymers were tested for polyquaternium-1 determination. When water-soluble BPLPs are hybrid with polyquaternium-1, the formed complex may be both water soluble complex and water-insoluble. a shift of fluorescence emission wavelength. If the complex is water-insoluble, the complex will be isolated from the aqueous solution first and then re-suspended in water or a organic solvent for fluorescence measurements. A standard curve will be established using a series of known concentration of polyquaternium-1. If the complex is still water-soluble, the protocol of trypan blue method was followed.

If water-insoluble BPLPs are used, BPLP organic solutions will be mixed with polyquaternium-1 aqueous solution. The kelating process may result in the transfer of polyquaternium-1 from water phase into organic phase. The organic phase was collected to do the fluorescence measurements. If the complex remains in the water phase, the water phase was collected for fluorescence measurements. To detect which phase the complex stays, FTIR analysis or HPLC was performed.

For water soluble complex, alternatively, HPLC was used to obtain pure BPLPpolyquaternium-1 complex which was be subjected to the fluorescence measurements. The isolation was obtainable since the size of the complex should be different from both BPLP and polyquaternium-1. Dialysis could be used to purify the BPLPpolyquaternium-1.

The present invention describes the discovery of a family of aliphatic biodegradable photoluminescent polymers (BPLPs and CBPLPs) that emit tunable, strong, and stable fluorescence. The synthesis of BPLPs and CBPLPs was straightforward and cost-effective. BPLP families possess excellent processability for micro/nano fabrication and desired mechanical properties, potentially serving as implant materials and bioimaging probes in vitro and in vivo. The data shows that the CBPLPs support cell attachment in vitro and only exert weak chronic inflammation in vivo. The development of BPLPs and CBPLPs represent a new direction in developing biodegradable materials and may have wide impact on basic sciences and a broad range of applications such as tissue engineering, drug delivery, and bioimaging.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

US 2002/0193522 A1: Synthesis and luminescent characteristics of novel phosphorus containing light-emitting polymers.

WIPO Patent Application No. WO/2007/143209: Luminescent Diketonate Polymers.

U.S. Pat. No. 7,345,596: Smart polymeric multiplayer sensors.

US Patent Application No. 2002/0018843 A1: Detection of biological molecules using chemical amplification and optical sensors.

1 Brus L. (1991) Quantum crystallites and nonlinear optics. *Appl Phys A-Mater* 53: 465-474.

2 Nirmal M. Brus L. (1999) Luminescence photophysics in semiconductor nanocrystals. *Accounts Chem Res* 32: 407-414.

3 Klimov V L, et al. (2000) Optical gain and stimulated emission in nanocrystal quantum dots. *Science* 290: 314-317.

4 Coe S, Woo W K. Bawendi M G. (2002) Electroluminescence from single monolayers of nanocrystals in molecular organic devices. *Nature* 420: 800-803.

5 Wozniak A K, et al. (2008) Single-molecule FRET measures bends and kinks in DNA. *Proc Natl Acad USA* 105: 18337-18342.

6 Wang H, et al. (2005) In vitro and in vivo two-photon luminescence imaging of single gold nanorods. *Proc Natl Acad USA* 102: 15752-15756.

7 Waggoner A. (2006) Fluorescent labels for proteomics and genomics. *Curr Opin Chem Biol* 10: 62-66.

8 Lopez-Crapez E, et al. (2008) A homogeneous resonance energy transfer-based assay to monitor MutS/DNA interactions. *Anal Biochem* 383: 301-306.

9 Thurn K T, et al. (2007) Nanoparticles for applications in cellular imaging. *Nanoscale Res Lett* 2: 430-441.

10 Wang F, et al. (2006) Luminescent nanomaterials for biological labelling. *Nanotechnology* 17: R1-R13.

11 Gao X, et al. (2005) In vivo molecular and cellular imaging with quantum dots. *Curr Opin Biotech* 16: 63-72.

12 Jamieson T, et al. (2007) Biological applications of quantum dots. *Biomaterials* 28: 4717-4732.

13 Michalet X, et al. (2005) Quantum dots for live cells, in vivo imaging, and diagnostics. *Science* 307: 538-544.

14 Su J, et al. (2008) Exploring feasibility of multicolored CdTe quantum dots for in vitro and in vivo fluorescent imaging. *J Nanosci Nanotechnol* 8: 1174-1177.

15 Mauring K, Krasnenko V. Miller S. (2007) Photophysics of the blue fluorescent protein. *J Lumin* 122: 291-293.

16 Yanushevich Y G, et al. (2002) A strategy for the generation of non-aggregating mutants of Anthozoa fluorescent proteins. *FEBS L* 511: 11-14.

17 Nie S M, Xing Y, Kim G J. Simons J W. (2007) Nanotechnology applications in cancer. *Annu Rev Biomed Eng* 9: 257-288.

18 Mancini M C, Kairdolf B A, Smith A M. Nie S. (2008) Oxidative quenching and degradation of polymer-encap- 18 sulated quantum dots: new insights into the long-term fate and toxicity of nanocrystals in vivo. *J Am Chem Soc* 130: 10836.
19 Huang S P, Huang G S. Chen S A. (2007) Deep blue electroluminescent phenylene-based polymers. *Synthetic Met* 157: 863-871.
20 Gaumet M, Gurny R. Delie F. (2007) Fluorescent biodegradable PLGA particles with narrow size distributions: Preparation by means of selective centrifugation. *Int J Pharm* 342: 222-230.
21 Ogura Y. Kimura H. (1995) Biodegradable Polymer Microspheres for Targeted Drug-Delivery to the Retinal-Pigment Epithelium. *Surv Ophthalmol* 39: SI7-S24.
22 Ghoroghchian P P, et al. (2007) Controlling bulk optical properties of emissive polymersomes through intramembraneous polymer-fluorophore interactions. *Chem Mater* 19: 1309-1318.
23 Rhyner M N, et al. (2006) Quantum dots and multifunctional nanoparticles: new contrast agents for tumor imaging. *Nanomedicine* 1: 209-217.
24 Yang J, et al. (2006) Synthesis and evaluation of poly(diol citrate) biodegradable elastomers. *Biomaterials* 27: 1889-1898.
25 Yang J, Webb A R. Ameer G A. (2004) Novel citric acid-based biodegradable elastomers for tissue engineering. *Adv Mater* 16: 511-516.
26 Mulliken R S. (1939) Intensities of Electronic Transitions in Molecular Spectra IV. Cyclic Dienes and Hyperconjugation. *J Chem Phys* 7: 339-352.
27 Bruggeman J P, et al. (2008) Biodegradable xylitol-based polymers. *Adv Mater* 20: 1922-1927.
28 Wang Y, Ameer G A, Sheppard B J. Langer R. (2002) A tough biodegradable elastomer. *Nature Biotechnology* 20: 602-606.
29 Yang J, et al. (2006) Modulating expanded polytetrafluoroethylene vascular graft host response via citric acid-based biodegradable elastomers. *Advanced Materials* 18: 1493-1498.
30 Yang J, Motlagh D, Webb A R. Ameer G A. (2005) Novel biphasic elastomeric scaffold for small-diameter blood vessel tissue engineering. *Tissue Eng* 11: 1876-1886.
31 Yang J, et al. (2008) Fluorescent magnetic nanohybrids as multimodal imaging agents for human epithelial cancer detection. *Biomaterials* 29: 2548-2555.
32 Altschuh D, Oncul S. Demchenko A P. (2006) Fluorescence sensing of intermolecular interactions and development of direct molecular biosensors. *J Mol Recognit* 19: 459-477.
33 Langer R. Vacanti J P. (1993) Tissue Engineering. *Science* 260: 920-926.
34 Levenberg S. Langer R. (2004) Advances in tissue engineering. *Curr Top Dev Biol biology* 61: 113-134.
35 Nijst C L, et al. (2007) Synthesis and characterization of photocurable elastomers from poly(glycerol-co-sebacate). *Biomacromolecules* 8: 3067-3073.
36 Yang J, et al. (2002) Fabrication and surface modification of macroporous poly(L-lactic acid) and poly(L-lactic-co-glycolic acid) (70/30) cell scaffolds for human skin fibroblast cell culture. *J Biomed Mater Res* 62: 438-446.
37 Williams A T R, Winfield S A. Miller J N. (1983) Relative fluorescence quantum yields using a computer-controlled luminescence spectrometer. *Analyst* 108: 1067-1071
38 Timmer M, et al. (2003) In vitro cytotoxicity of injectable and biodegradable poly(propylene fumarate)-based networks: unreacted macromers, cross-linked networks, and degradation products. *Biomacromolecules* 4: 1026-1033.
39 Zhang J, et al. (2008) Evaluation of red CdTe and near infrared CdHgTe quantum dots by fluorescent imaging. *J Nanosci Nanotechnol* 8: 1155-1159.
40. Webb, A R, Yang, J, and Ameer, G A, *Biodegradable polyester elastomers in tissue engineering.* Expert Opinion on Biological Therapy, 2004. 4(6): p. 801-812.
41. Gachkovskii, V F, Fluorescence spectra of photoreduced forms of chlorophyll and pheophytin. Biofizika, 1959. 4(1): p. 19-26.
42. Fillinger, M F, Sampson, L N, Cronenwett, J L, Powell, R J, and Wagner, R J, *Coculture of endothelial cells and smooth muscle cells in bilayer and conditioned media models.* J Surg Res, 1997. 67(2): p. 169-78.
43. Imberti, B, Seliktar, D, Nerem, R M, and Remuzzi, A, *The response of endothelial cells to fluid shear stress using a co-culture model of the arterial wall.* Endothelium-New York, 2002. 9(1): p. 11-23.
44. Ziegler, T, Alexander, R W, and Nerem, R M, *An endothelial cell-smooth muscle cell coculture model for use in the investigation of flow effects on vascular biology.* Ann Biomed Eng, 1995. 23(3): p. 216-25.
45. Williams, C and Wick, T M, *Endothelial cell-smooth muscle cell co-culture in a perfusion bioreactor system.* Annals of Biomedical Engineering, 2005. 33(7): p. 920-928.
46. Powell, R J, Hydowski, J, Frank, O, Bhargava, J, and Sumpio, B E, *Endothelial cell effect on smooth muscle cell collagen synthesis.* Journal of Surgical Research, 1997. 69(1): p. 113-118.
47. Chiu, J J, Chen, L J, Chen, C N, Lee, P L, and Lee, C I, *A model for studying the effect of shear stress on interactions between vascular endothelial cells and smooth muscle cells.* Journal of Biomechanics, 2004. 37(4): p. 531-539.
48. Chiu, J J, Chen, L J, Lee, P L, Lee, C I, Lo, L W, Usami, S, and Chien, S, *Shear stress inhibits adhesion molecule expression in vascular endothelial cells induced by coculture with smooth muscle cells.* Blood, 2003. 101(7): p. 2667-2674.
49. Mathew, J, Kache, V, Liu, C, Tang, L, and Yang, J, *Nano-featured highly interconnective macroporous elastic scaffolds for cardiovascular tissue engineering* IEEE Dallas Engineering in Medicine and Biology Workshop (IEEE Xplore online publication), 2007: p. 43-46.
50. McGonigle, E A, Liggat, J J, Pethrick, R A, Jenkins, S D, Daly, J H, and Hayward, D, *Permeability of N-2, Ar, He, O-2 and CO2 through biaxially oriented polyester films-dependence on free volume.* Polymer, 2001. 42(6): p. 2413-2426.
51. Yang, J, Wan, Y Q, Yang, J L, Bei, J Z, and Wang, S G, *Plasma-treated, collagen anchored polylactone: Its cell affinity evaluation under shear or shear-free conditions.* Journal of Biomedical Materials Research Part A, 2003. 67A(4): p. 1139-1147.
52. Williams, C and Wick, T M, *Perfusion bioreactor for small diameter tissue engineered arteries.* Tissue Engineering, 2004. 10(5/6): p. 930-941.
53. Woessner, J F, *Citation Classic—Determination of Hydroxyproline in Tissue and Protein Samples Containing Small Proportions of This Imino Acid.* Current Contents/Life Sciences, 1980(2): p. 10-10.
54. Farndale, R W, Sayers, C A, and Barrett, A J, *A direct spectrophotometric microassay for sulfated glycosaminoglycans in cartilage cultures.* Connect Tissue Res, 1982. 9(4): p. 247-8.
55. Kaushal, S, Amiel, G E, Guleserian, K J, Shapira, O M, Perry, T, Sutherland, F W, Rabkin, E, Moran, A M, Schoen, F J, Atala, A, Soker, S, Bischoff, J, and Mayer, J E, *Functional small-diameter neovessels created using endothelial progenitor cells expanded ex vivo.* Nature Medicine, 2001. 7(9): p. 1035-1040.
56. Niklason, L E, Abbott, W, Gao, J M, Klagges, B, Hirschi, K K, Ulubayram, K, Conroy, N, and Jones, R, *Morphologic and mechanical characteristics of engineered bovine arteries.* Journal of Vascular Surgery, 2001. 33(3): p. 628-638.
57. Isaka, M, Nishibe, T, Okuda, Y, Saito, M, Seno, T, Yamashita, K, Izumisawa, Y, Kotani, T, and Yasuda, K, *Experimental study on stability of a high porosity expanded polytetrafluoroethylene graft in dogs.* Ann Thorac Cardiovasc Surg, 2006. 12(1): p. 37-41.
58. Xu, J, Ge, H, Zhou, X, Yang, D, Guo, T, He, J, Li, Q, and Hao, Z, *Tissue-engineered vessel strengthens quickly under physiological deformation: application of a new perfusion bioreactor with machine vision.* J Vasc Res, 2005. 42(6): p. 503-8.

The invention claimed is:

1. A polymer composition comprising:
    an oligomer synthesized from monomers comprising (i) a multifunctional monomer comprising citric acid or triethyl citrate, (ii) a diol, and (iii) an amino acid, wherein the amino acid is linked as a side group to the oligomer backbone.

2. The composition of claim 1, wherein the diol is selected from 1,8-octanediol, ethylene glycol, propylene glycol, poly(ethylene glycol), polypropylene glycol), 1,3-propanediol, ethanediol, and cis-1,2-cyclohexanediol.

3. The composition of claim 1, wherein the amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof.

4. The composition of claim 1, wherein the amino acid comprises an L-amino acid, D-amino acid, D,L-amino acid, or a derivative thereof.

5. The composition of claim 1, wherein an acid anhydride or a multifunctional acid chloride is used in addition to the citric acid or triethyl citrate.

6. The composition of claim 1, wherein maleic acid, maleic anhydride, fumaric acid, fumaryl chloride, acryloylchloride, itaconic acid, or allylmalonic acid is used in addition to the citric acid or triethyl citrate.

7. The composition of claim 1, wherein the oligomer is crosslinked.

8. A composition comprising:
    an oligomer synthesized from monomers comprising (i) a multifunctional monomer comprising citric acid or triethyl citrate, (ii) a diol, (iii) an amino acid, and (iv) a di-isocyanate wherein the amino acid is linked as a side group to the oligomer backbone.

9. The composition of claim 8, wherein the multifunctional monomer comprises citric acid.

10. The composition of claim 8, wherein the diol is selected from 1,8-octanediol, ethylene glycol, propylene glycol, poly(ethylene glycol), poly(propylene glycol), 1,3-propanediol, ethanediol, and cis-1,2-cyclohexanediol.

11. The composition of claim 8, wherein the amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof.

12. The composition of claim 8, wherein the amino acid comprises an L-amino acid, D-amino acid, D,L-amino acid, or a derivative thereof.

13. The composition of claim 8, wherein the multifunctional monomer comprises citric acid, the diol comprises 1,8-octanediol, the amino acid comprises cysteine or serine, and the di-isocyanate comprises hexamethylene-1,6-di-isocyanate or 1,4-butane-di-isocyanate.

14. A method of making a crosslinked urethane-doped biodegradable photoluminescent polyester (CUBPLP) comprising:
    mixing (i) a multifunctional monomer comprising citric acid or triethyl citrate and (ii) a diol to form a mixture;
    raising the temperature of the mixture to melt the mixture;
    lowering the temperature of the mixture with stirring to form an oligomer;
    adding an amino acid to the oligomer with stirring to form a pre-BPLP-amino acid;
    purifying the pre-BPLP-amino acid;
    dissolving the purified pre-BPLP-amino acid to form a solution;
    adding a di-isocyanate to the pre-BPLP-amino acid solution to form a pre-CUBPLP (UBPLP);
    casting a film of the pre-CUBPLP (UBPLP); and
    drying the pre-CUBPLP (UBPLP) film to obtain the CUBPLP.

15. The method of claim 14, wherein the diol is selected from 1,8-octanediol, ethylene glycol, propylene glycol, poly(ethylene glycol), poly(propylene glycol), 1,3-propanediol, ethanediol, and cis-1,2-cyclohexanediol.

16. The method of claim 14, wherein the multifunctional monomer comprises citric acid, the diol comprises 1,8-octanediol, the amino acid comprises cysteine or serine, and the di-isocyanate comprises hexamethylene-1,6-di-isocyanate or 1,4-butane-di-isocyanate.

17. The method of claim 14, wherein purifying the pre-BPLP-amino acid comprises:
    adding the pre-BPLP-amino acid to deionized water;
    collecting an undissolved pre-BPLP-amino acid portion from the deionized water; and
    lyophilizing the collected pre-BPLP-amino acid to obtain purified pre-BPLP-amino acid.

18. The method of claim 14, wherein dissolving the purified pre-BPLP-amino acid to form a solution comprises dissolving the purified pre-BPLP-amino acid in 1,4-dioxane.

19. The method of claim 14, wherein the film of the pre-CUBPLP (UBPLP) is cast in a laminar airflow.

20. The method of claim 14, wherein forming the pre-BPLP-amino acid solution further comprises adding one or more catalysts to the solution, the one or more catalysts being selected from tin octanoate, dibutyl tin dilaurate, and 1,4-diazabicyclo[2.2.2]octane.

* * * * *